(12) United States Patent
Nikolaidis et al.

(10) Patent No.: US 10,286,219 B2
(45) Date of Patent: May 14, 2019

(54) ELECTRICAL CERMET FEEDTHROUGH WITH ONE-PIECE FEEDTHROUGH ELEMENT HAVING PLURAL REGIONS

(71) Applicant: Heraeus Deutschland GmbH & Co. KG, Hanau (DE)

(72) Inventors: Ilias Nikolaidis, Hanau (DE); Frederik Roth, Bruchköbel (DE); Ulrich Hausch, Frankfurt (DE); Robert Dittmer, Hanau (DE); Jacqueline Gebhardt, Schwaikheim (DE); Sandra Sauer, Grossostheim (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 0 days.

(21) Appl. No.: 15/680,169

(22) Filed: Aug. 17, 2017

(65) Prior Publication Data

US 2018/0050212 A1 Feb. 22, 2018

(30) Foreign Application Priority Data

Aug. 17, 2016 (EP) .................................. 16184556

(51) Int. Cl.
*A61N 1/37* (2006.01)
*A61N 1/375* (2006.01)
(Continued)

(52) U.S. Cl.
CPC ............ *A61N 1/3754* (2013.01); *A61B 5/686* (2013.01); *A61L 27/10* (2013.01); *B28B 11/243* (2013.01);
(Continued)

(58) Field of Classification Search
CPC ....... A61N 1/3754; A61B 5/686; A61L 27/10; B28B 11/243; H05K 5/0095; H05K 5/0247; H02G 3/18
(Continued)

(56) References Cited

U.S. PATENT DOCUMENTS 7,164,572 B1 *   1/2007   Burdon ................ A61N 1/3754
                                                          361/302
9,504,840 B2 *  11/2016   Pavlovic .............. A61N 1/3754
(Continued)

*Primary Examiner* — Dhirubhai R Patel
(74) *Attorney, Agent, or Firm* — Dicke, Billig & Czaja, PLLC

(57) ABSTRACT

One aspect relates to an apparatus includes a ceramic body including a first surface and a further surface. The first surface is opposite the further surface, the first surface includes a first opening. The further surface includes a further opening. The first opening and the further opening are connected by a tunnel, which at least partly includes a tunnel filling and is occluded by the tunnel filling. The tunnel filling includes a first constituent, including a cermet, and a second constituent. The first and second constituents are electroconductingly connected to one another. The first constituent has a first electrical conductivity and the second constituent has a second electrical conductivity, which differs from the first by at least $5 \cdot 10^{-4}$ Siemens per meter (S/m). The ceramic body is characterized by a further electrical conductivity. The first electrical conductivity is more by at least $1 \cdot 10^5$ Siemens per meter (S/m) than the 15 further electrical conductivity.

16 Claims, 10 Drawing Sheets

(51) Int. Cl.
  *A61B 5/00* (2006.01)
  *A61L 27/10* (2006.01)
  *B28B 11/24* (2006.01)
  *H05K 5/00* (2006.01)
  *H05K 5/02* (2006.01)
  *A61B 5/0402* (2006.01)

(52) U.S. Cl.
  CPC ......... *H05K 5/0095* (2013.01); *H05K 5/0247* (2013.01); *A61B 5/0402* (2013.01)

(58) Field of Classification Search
  USPC ....................................................... 174/506
  See application file for complete search history.

(56) References Cited

U.S. PATENT DOCUMENTS

| | | |
|---|---|---|
| 2012/0193117 A1 | 8/2012 | Specht et al. |
| 2012/0193125 A1 | 8/2012 | Pavlovic et al. |
| 2015/0165219 A1 | 6/2015 | Markham et al. |

* cited by examiner

ELECTRICAL CERMET FEEDTHROUGH WITH ONE-PIECE FEEDTHROUGH ELEMENT HAVING PLURAL REGIONS

CROSS-REFERENCE TO RELATED APPLICATIONS

This Utility Patent Application claims priority to European Patent Application No. EP 16184556.5, filed on Aug. 17, 2016, which is incorporated herein by reference.

BACKGROUND

One aspect relates to an apparatus comprising a ceramic body having a tunnel and a tunnel filling, comprising a first constituent and a second constituent, wherein the electrical conductivity of the first constituent and of the second constituent differs by at least $5 \cdot 10^4$ S/m; a further apparatus, especially a precursor of the preceding apparatus, especially a green body; a method, especially for producing an electrical feedthrough or a green body of an electrical feedthrough; a ceramic precursor, especially a green body, obtainable by the aforesaid method; a further apparatus, especially an electrical feedthrough, obtainable by the aforesaid method; an electrical device, especially an implantable electrical medical device; a use of an aforesaid apparatus; a use of the aforesaid ceramic precursor; a method comprising implanting the aforesaid implantable electrical medical device; and a use of the aforesaid implantable electrical medical device.

Disclosed in the prior art are numerous implantable electrical medical devices, as for example pacemakers, defibrillators and electrocardiographs (ECG devices). The known pacemakers include bladder pacemakers, respiratory pacemakers, intestinal pacemakers, diaphragmatic pacemakers, cerebral pacemakers and, for example, cardiac pacemakers. Such devices are typically implanted into a human animal organism in order to therapeutize, treat or monitor a disease or dysfunction of the organism. For this purpose there must always be an electrical connection between the device interior and the surroundings of the device housing. For instance, a pacemaker when deployed is intended to generate an electrical voltage pulse in the interior of the pacemaker housing by way of an electrical pulse generator, and to deliver this pulse via an electrode outside the pacemaker housing to organic tissue of the patient. An implanted measuring device such as an ECG device or biomonitor records electrical voltage signals via measuring electrodes outside the device housing, and passes them into the housing for processing. In each case it is necessary to provide an electrical connection, often a multiplicity of electrical connections, between the interior and the surroundings of the housing. At the same time, however, it must be ensured that the housing interior is hermetically closed off from the organic surroundings. In the prior art, this is done using electrical feedthroughs. A prior-art electrical feedthrough includes an electrically conducting feedthrough element, typically a platinum wire or a pin, which extends from the device interior to the outside. The feedthrough element here is insulated electrically from the housing, which typically consists of a titanium alloy, typically by means of a ceramic ring. The required hermetic sealing of the feedthrough is typically achieved by welding a titanium flange into an opening of the housing and soldering or welding the ceramic ring into this flange. The feedthrough element is soldered into the ceramic ring with a gold solder. In order to achieve hermetic sealing, accordingly, numerous connections between different components and materials are produced in the prior art, using expensive materials such as the gold solder. This leads to very complicated and expensive production methods and also to disadvantages with regard to the reliability of the device. The various connection sites are potential sites of breakage and leakage. Leakage of an implanted electrical medical device, however, must be avoided at all costs. If such a device develops leakages, it may harm the patient, or the device fails and is no longer able to fulfil its function. This is particularly serious in view of the diseases to be treated by a pacemaker, such as heart conditions, for example. Even if defects in the device are recognized promptly, the replacement of the device implies a considerable surgical intervention into the patient's body.

In this connection, cermet feedthroughs exhibit considerable advantages. They are produced by introducing a feedthrough channel in a green ceramic compact with a cermet paste and firing the two together. Accordingly, the ceramic insulating body and the electrically conducting feedthrough element are produced in one piece without inter-material connections. In order to achieve a suitable density of the cermet feedthrough element, a suitable thermal expansion behaviour and effective bonding to the ceramic body, it is advantageous to use a cermet having not too a high metal fraction, typically a fraction of platinum. In order then for the cermet feedthrough element to be able to be utilized as such, it must be contacted electrically at both ends, in the housing interior and on the side facing the patient body, by means of soldering, bonding or welding. For successful such electrical connection, a surface with an increased metal fraction and/or an increased electrical conductivity is needed on the feedthrough element. In the prior art, such a surface is applied subsequently, additionally, to the feedthrough element, by means, for example, of the printing of a paste and subsequent firing or sintering, by means of thermal spraying, or by means of thin-film coating. In each case, additional method steps on each side of the feedthrough element produce at least one additional inter-material connection. This, however, runs exactly counter to the fundamental concept of a one-piece cermet feedthrough. The production process for the prior-art cermet feedthrough therefore becomes more complicated and more expensive. Furthermore, the additional connection points render the prior-art feedthrough less mechanically robust and durable.

For these and other reasons, a need exists for the present embodiments.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1A:
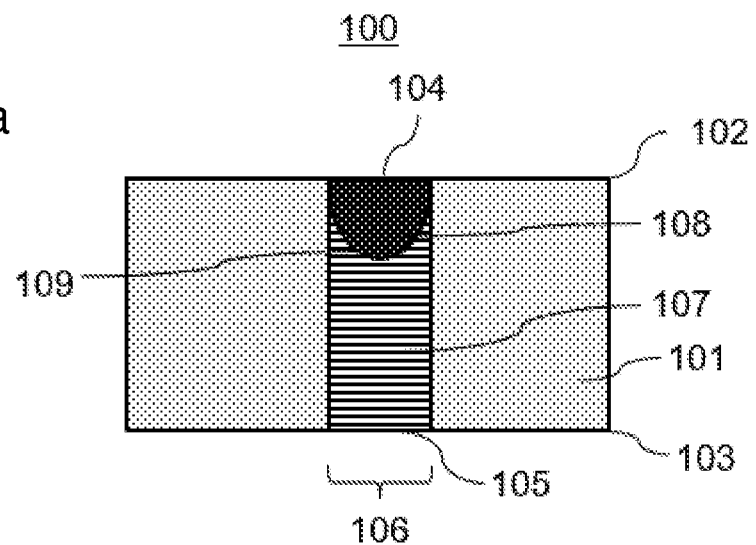
FIG. 1a illustrates a diagrammatic cross section through an apparatus of one embodiment.

In the following Detailed Description, reference is made to the accompanying drawings, which form a part hereof, and in which is shown by way of illustration specific embodiments in which the embodiment may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiment is defined by the appended claims.

It is to be understood that the features of the various exemplary embodiments described herein may be combined with each other, unless specifically noted otherwise.

One embodiment overcomes at least partly a disadvantage which arises from the prior art. One embodiment provides an electrically contactable electrical feedthrough, more particularly a cermet feedthrough, having enhanced mechanical robustness, particularly of electrical contact points. One embodiment provides an electrically contactable electrical feedthrough, more particularly a cermet feedthrough, consisting of fewer individual parts. One embodiment provides an electrically contactable electrical feedthrough, more particularly a cermet feedthrough, comprising fewer connection points between different materials. One embodiment provides an electrically contactable electrical feedthrough, more particularly a cermet feedthrough, which is less complicated to produce or can be produced in fewer method steps, or both. One embodiment provides an electrically contactable electrical feedthrough, more particularly a cermet feedthrough, which has a more compact construction. One embodiment provides an electrically contactable electrical feedthrough, more particularly a cermet feedthrough, which has a combination of two or more of the above advantages. One embodiment provides an implantable electrical medical device which includes an electrical feedthrough having at least one of the above advantages. One embodiment provides an implantable electrical medical device having an extended operating time or lifetime. One embodiment provides an implantable electrical medical device which is less susceptible to faults in use in a human body. One embodiment provides an implantable electrical medical device which works more reliably in a human body.

A contribution to achieving at least one of the above is made by an embodiment 1 of an apparatus 1, comprising a ceramic body, comprising a first surface and a further surface; wherein the first surface is opposite the further surface; wherein the first surface includes a first opening; wherein the further surface includes a further opening; wherein the first opening and the further opening are connected by a tunnel; wherein the tunnel at least partly includes a tunnel filling and is occluded by the tunnel filling; wherein the tunnel filling includes a first constituent and a second constituent; wherein the first constituent includes a cermet; wherein the first constituent and the second constituent are electroconductingly connected to one another; wherein a surface of the tunnel filling that faces the further opening is at least partly a surface of the second constituent; wherein the first constituent is characterized by a first electrical conductivity; wherein the second constituent is characterized by a second electrical conductivity; wherein the ceramic body is characterized by a further electrical conductivity; wherein the first electrical conductivity is more by at least $1 \cdot 10^5$ S/m, in one embodiment by at least $5 \cdot 10^5$ S/m, in one embodiment by at least $1 \cdot 10^6$ S/m, than the further electrical conductivity; wherein the second electrical conductivity differs from the first electrical conductivity by at least $5 \cdot 10^4$ S/m, in one embodiment by at least $1 \cdot 10^5$ S/m, in one embodiment by at least $2.5 \cdot 10^5$ S/m.

An inventive embodiment 2 of the apparatus 1 is designed according to embodiment 1, wherein the second electrical conductivity is more than the first electrical conductivity.

An inventive embodiment 3 of the apparatus 1 is designed according to embodiment 1 or 2, wherein the first constituent has a first metal fraction, based on the weight of the first constituent; wherein the second constituent has a second metal fraction, based on the weight of the second constituent; wherein the second metal fraction is more by at least 5 wt %, in one embodiment by at least 10 wt %, in one embodiment by at least 15 wt %, than the first metal fraction.

An inventive embodiment 4 of the apparatus 1 is designed according to one of the preceding embodiments, wherein the tunnel filling includes a third constituent; wherein the third constituent is electroconductingly connected to the first constituent or to the second constituent or to both; where a surface of the tunnel filling that faces the first opening is at least partly a surface of the third constituent; wherein the third constituent is characterized by a third electrical conductivity; wherein the third electrical conductivity differs from the first electrical conductivity by at least $5 \cdot 10^4$ S/m, in one embodiment by at least $1 \cdot 10^5$ S/m, in one embodiment by at least $2.5 \cdot 10^5$ S/m.

An inventive embodiment 5 of the apparatus 1 is designed according to embodiment 4, wherein the third electrical conductivity is more than the first electrical conductivity.

An inventive embodiment 6 of the apparatus 1 is designed according to embodiment 4 or 5, wherein the first constituent has a first metal fraction, based on the weight of the first constituent; wherein the third constituent has a third metal fraction, based on the weight of the third constituent; wherein the third metal fraction is more by at least 5 wt %, in one embodiment by at least 10 wt %, in one embodiment by at least 15 wt %, than the first metal fraction.

An inventive embodiment 7 of the apparatus 1 is designed according to one of the preceding embodiments, wherein the tunnel fully includes the first constituent and the second constituent, or the first constituent and the second constituent and the third constituent. In other words, the respective constituents do not protrude from the first opening or the further opening or both.

An inventive embodiment 8 of the apparatus 1 is designed according to one of the preceding embodiments, wherein the surface of the tunnel filling that faces the further opening has a distance of less than 3 mm, in one embodiment of less than 2 mm, in one embodiment of less than 1 mm, in one embodiment of less than 800 µm, in one embodiment of less than 600 µm, in one embodiment of less than 400 µm, in one embodiment of less than 200 µm, from the further opening. The surface of the tunnel filling that faces the further opening in one embodiment has the distance from the further opening in the direction of the first opening, in other words in the direction into the tunnel.

An inventive embodiment 9 of the apparatus 1 is designed according to one of embodiments 4 to 8, wherein the surface of the tunnel filling that faces the first opening has a distance of less than 3 mm, in one embodiment of less than 2 mm, in one embodiment of less than 1 mm, in one embodiment of less than 800 µm, in one embodiment of less than 600 µm, in one embodiment of less than 400 µm, in one embodiment of less than 200 µm, from the first opening. The surface of the tunnel filling that faces the first opening in one embodiment has the distance from the first opening in the direction of the further opening, in other words in the direction into the tunnel.

An inventive embodiment 10 of the apparatus 1 is designed according to one of the preceding embodiments, wherein the second electrical conductivity or the third electrical conductivity or both is or are in a range from $1 \cdot 10^3$ to $1 \cdot 10^7$ S/m, in one embodiment from $1 \cdot 10^4$ to $1 \cdot 10^7$ S/m, in one embodiment from $1 \cdot 10^6$ to $1 \cdot 10^7$ S/m.

An inventive embodiment 11 of the apparatus 1 is designed according to one of the preceding embodiments, wherein the second constituent or the third constituent or both are connected to an electrical conductor. In one embodiment, an electrical conductor is a wire or a solder or both. The electrical conductor is in one embodiment connected to the second constituent or the third constituent or both by one selected from the group consisting of bonding, welding and soldering, or a combination of at least two thereof. The electrical conductor is in one embodiment not included by the tunnel.

An inventive embodiment 12 of the apparatus 1 is designed according to one of the preceding embodiments, wherein one selected from the group consisting of the first constituent, the second constituent and the third constituent, or a combination of at least two thereof, is a cermet.

An inventive embodiment 13 of the apparatus 1 is designed according to one of the preceding embodiments, wherein the first constituent forms a first constituent layer; wherein the second constituent forms a second constituent layer; wherein the second constituent layer overlays the first constituent layer.

An inventive embodiment 14 of the apparatus 1 is designed according to one of the preceding embodiments, wherein the first constituent includes a concave first constituent surface; wherein the second constituent includes a convex second constituent surface, with the convex second constituent surface overlaying the concave first constituent surface. Also possible in this connection is a conelike embodiment of the second constituent. In that case, the second constituent surface is a conical surface and the first constituent surface is inverse to it, in one embodiment funnel-shaped.

An inventive embodiment 15 of the apparatus 1 is designed according to one of the embodiments 1 to 13, wherein the first constituent includes a convex first constituent surface; wherein the second constituent includes a concave second constituent surface, with the concave second constituent surface overlaying the convex first constituent surface. Also possible in this connection is an embodiment of the first constituent surface as a conical surface. In that case, the second constituent surface is inverse thereto, in one embodiment funnel-shaped.

An inventive embodiment 16 of the apparatus 1 is designed according to one of the embodiments 3 to 15, wherein the first constituent forms a first constituent layer; wherein the third constituent forms a third constituent layer; wherein the first constituent layer overlays the third constituent layer.

An inventive embodiment 17 of the apparatus 1 is designed according to one of embodiments 3 to 16, wherein the first constituent includes a concave further first constituent surface; wherein the third constituent includes a convex third constituent surface; wherein the concave further first constituent surface overlays the convex third constituent surface. Also possible in this context is a conical design of the third constituent. In that case the third constituent surface is a lateral cone surface, and the further first constituent surface is an inverse thereof, in one embodiment funnel-shaped.

An inventive embodiment 18 of the apparatus 1 is designed according to one of embodiments 3 to 16, wherein the first constituent includes a convex further first constituent surface; wherein the third constituent includes a concave third constituent surface; wherein the convex further first constituent surface overlays the concave third constituent surface. Also possible in this context is a design of the further first constituent surface as a lateral cone surface. In that case the third constituent surface is the inverse thereof, in one embodiment funnel-shaped.

An inventive embodiment 19 of the apparatus 1 is designed according to one of the preceding embodiments, wherein the ceramic body and the first constituent and the second constituent, or the ceramic body and the first constituent and the second constituent and the third constituent, are formed as one piece. In one embodiment, the ceramic body and the first constituent and the second constituent, or the ceramic body and the first constituent and the second constituent and the third constituent, are sintered from a single green body.

A contribution to achieving at least one of the above is made by an embodiment 1 of an apparatus 2, comprising a first ceramic precursor layer and a second ceramic precursor layer,
 a) wherein for the first ceramic precursor layer it is at least the case that:
  i) the first ceramic precursor layer includes a first layer surface and a further layer surface,
  ii) the first layer surface is opposite the further layer surface,
  iii) the first layer surface includes a first opening,
  iv) the further layer surface includes a further opening,
  v) the first opening and the further opening are connected by a first tunnel,
  vi) the first tunnel includes a first tunnel filling at least partly and is occluded by the first tunnel filling,
  vii) the first tunnel filling includes a first composition and a second composition, viii) a surface of the first tunnel filling that faces the further opening is at least partly a surface of the second composition,
ix) the first composition has a first composition metal fraction, based on the weight of the first composition,
x) the second composition has a second composition metal fraction, based on the weight of the second composition, and
xi) the second composition metal fraction differs by at least 3 wt %, in one embodiment at least 7 wt %, in one embodiment at least 15 wt %, from the first composition metal fraction,
b) wherein for the second ceramic precursor layer it is at least the case that:
i) the second ceramic precursor layer includes a first layer surface and a further layer surface,
ii) the first layer surface is opposite the further layer surface,
iii) the first layer surface includes a first opening,
iv) the further layer surface includes a further opening,
v) the first opening and the further opening are connected by a second tunnel,
vi) the second tunnel includes a second tunnel filling at least partly and is occluded by the second tunnel filling,
vii) the second tunnel filling includes a second first composition,
viii) the second first composition has a second first composition metal fraction, based on the weight of the second first composition, and
ix) the second composition metal fraction differs by at least 3 wt %, in one embodiment by at least 7 wt %, in one embodiment by at least 15 wt %, from the second first composition metal fraction,
c) wherein the further layer surface of the second ceramic precursor layer is in contact with the first layer surface of the first ceramic precursor layer in such a way that the first tunnel filling and the second tunnel filling are in contact. In one embodiment, the first ceramic precursor layer is laminated onto the second ceramic precursor layer or vice versa, or both.

An inventive embodiment 2 of the apparatus 2 is designed according to embodiment 1, wherein the device further includes a third ceramic precursor layer, wherein the third ceramic precursor layer includes a first layer surface and a further layer surface, wherein the first layer surface is opposite the further layer surface, wherein the first layer surface includes a first opening, wherein the further layer surface includes a further opening, wherein the first opening and the further opening are connected by a third tunnel, wherein the third tunnel at least partly includes a third tunnel filling and is occluded by the third tunnel filling, wherein the third tunnel filling includes a third first composition and a further second composition, wherein a surface of the third tunnel filling that faces the first opening is at least partly a surface of the further second composition, wherein the third first composition has a third first composition metal fraction, based on the weight of the third first composition, wherein the further second composition has a further second composition metal fraction, based on the weight of the further second composition, wherein the further second composition metal fraction differs by at least 3 wt %, in one embodiment by at least 7 wt %, in one embodiment by at least 15 wt %, from the third first composition metal fraction, wherein the first layer surface of the second ceramic precursor layer is overlaid by the further layer surface of the third ceramic precursor layer.

A contribution to achieving at least one of the above is made by an embodiment 1 of an apparatus 3, comprising a ceramic precursor layer, wherein for the ceramic precursor layer it is at least the case that:
a) the ceramic precursor layer includes a first layer surface and a further layer surface,
b) the first layer surface is opposite the further layer surface,
c) the first layer surface includes a first opening,
d) the further layer surface includes a further opening,
e) the first opening and the further opening are connected by a tunnel,
f) the tunnel includes a tunnel filling at least partly and is occluded by the tunnel filling,
g) the tunnel filling includes a first composition, a second composition and a third composition,
h) a surface of the tunnel filling that faces the further opening is at least partly a surface of the second composition,
i) a surface of the tunnel filling that faces the first opening is at least partly a surface of the third composition,
j) the first composition has a first composition metal fraction, based on the weight of the first composition,
k) the second composition has a second composition metal fraction, based on the weight of the second composition,
l) the third composition has a third composition metal fraction, based on the weight of the third composition, and
m) the second composition metal fraction or the third composition metal fraction or both differs or differ by at least 3 wt %, in one embodiment by at least 7 wt %, in one embodiment by at least 15 wt %, from the first composition metal fraction.

An inventive embodiment 3 of the apparatus 2 is designed according to embodiment 1 or 2, and an inventive embodiment 2 of the apparatus 3 is designed according to embodiment 1, wherein one selected from the group consisting of the first composition, the second first composition, the third first composition, the second composition, the further second composition, and the third composition, or a combination of at least two thereof, is a cermet paste.

A contribution to achieving at least one of the above is made by an embodiment 1 of a method 1, comprising as method steps
a) providing a first ceramic precursor layer comprising a first layer surface and a further layer surface, wherein the first layer surface is opposite the further layer surface, wherein the first layer surface includes a first opening, wherein the further layer surface includes a further opening, wherein the first opening and the further opening are connected by a first tunnel, wherein the first tunnel at least partly includes a first tunnel filling and is occluded by the first tunnel filling, wherein the first tunnel filling includes a first composition and a second composition, where a surface of the first tunnel filling that faces the further opening is at least partly a surface of the second composition, wherein the first composition has a first composition metal fraction, based on the weight of the first composition, wherein the second composition has a second composition metal fraction, based on the weight of the second composition, wherein the second composition metal fraction differs by at least 3 wt %, in one embodiment by at least 7 wt %, in one embodiment by at least 15 wt %, from the first composition metal fraction;

b) providing a second ceramic precursor layer, comprising a first layer surface and a further layer surface, wherein the first layer surface is opposite the further layer surface, wherein the first layer surface includes a first opening, wherein the further layer surface includes a further opening, wherein the first opening and the further opening are connected by a second tunnel, wherein the second tunnel at least partly includes a second tunnel filling and is occluded by the second tunnel filling, wherein the second tunnel filling includes a second first composition, wherein the second first composition has a second first composition metal fraction, based on the weight of the second first composition, wherein the second composition metal fraction differs by at least 3 wt %, in one embodiment by at least 7 wt %, in one embodiment by at least 15 wt %, from the second first composition metal fraction; and c) contacting the further layer surface of the second ceramic precursor layer with the first layer surface of the first ceramic precursor layer, so that the first tunnel filling and the second tunnel filling are contacted.

An inventive embodiment 2 of the method 1 is designed according to embodiment 1, wherein before method step c) a third ceramic precursor layer is provided, wherein the third ceramic precursor layer includes a first layer surface and a further layer surface, wherein the first layer surface is opposite the further layer surface, wherein the first layer surface includes a first opening, wherein the further layer surface includes a further opening, wherein the first opening and the further opening are connected by a third tunnel, wherein the third tunnel at least partly includes a third tunnel filling and is occluded by the third tunnel filling, wherein the third tunnel filling includes a third first composition and a further second composition, wherein a surface of the third tunnel filling that faces the first opening is a surface of the further second composition, wherein the third first composition has a third first composition metal fraction, based on the weight of the third first composition, wherein the further second composition has a further second composition metal fraction, based on the weight of the further second composition, wherein the further second composition metal fraction differs by at least 3 wt %, in one embodiment by at least 7 wt %, in one embodiment by at least 15 wt, from the third first composition metal fraction, wherein in method step c) the first layer surface of the second ceramic precursor layer is overlaid by the further layer surface of the third ceramic precursor layer.

An inventive embodiment 3 of the method 1 is designed according to embodiment 1 or 2, wherein in method step c) the first layer surface of the second ceramic precursor layer is overlaid by at least one further ceramic precursor layer in such a way that the at least one further ceramic precursor layer is positioned between the second ceramic precursor layer and the third ceramic precursor layer.

An inventive embodiment 4 of the method 1 is designed according to one of embodiments 1 to 3, wherein in method step c) the further layer surface of the second ceramic precursor layer is connected to the first layer surface of the first ceramic precursor layer by isostatic pressing. The isostatic pressing takes place in one embodiment in the course of lamination.

An inventive embodiment 5 of the method 1 is designed according to one of embodiments 1 to 4, wherein in method step a) the providing of the first ceramic precursor layer includes i) providing an unfilled first ceramic precursor layer, comprising the first layer surface and the further layer surface, wherein the first layer surface is opposite the further layer surface, wherein the first layer surface includes the first opening, wherein the further layer surface includes the further opening, wherein the first opening and the further opening are connected by the first tunnel;

ii) providing the first composition;

iii) introducing the first composition through the further opening into the first tunnel in at least one introduction step, wherein after each introduction step an introduced portion of the first composition is dried;

iv) providing the second composition; and v) overlaying the first composition in the first tunnel with the second composition in at least one introduction step, wherein after each introduction step an introduced portion of the second composition is dried.

In method step v), the first composition is in one embodiment overlaid in so many introduction steps with so many portions of the second composition as are necessary in order to fill the first tunnel completely and to occlude the further opening flush to the further layer surface.

An inventive embodiment 6 of the method 1 is designed according to embodiment 5, wherein in method step iii) the first composition is introduced in at least one first introduction step and a further introduction step through the further opening into the first tunnel, wherein in the first introduction step first of all a first portion of the first composition is introduced and thereafter in the further introduction step a further portion of the first composition is introduced, wherein the first portion of the first composition has a first viscosity, wherein the further portion of the first composition has a further viscosity, wherein the further viscosity is more than the first viscosity.

The further viscosity here is in one embodiment more by 40 Pa·s, in one embodiment by 50 Pa·s, in one embodiment by 60 Pa·s, than the first viscosity. The first portion in one embodiment has a first solids fraction and the further portion has a further solids fraction, wherein the further solids fraction is more than the first solids fraction. The further solids fraction here is in one embodiment more by at least 10 wt %, in one embodiment by at least 15 wt %, in one embodiment by at least 20 wt %, than the first solids fraction. In one embodiment, a solid in this case is a powder. In one embodiment, a powder is a ceramic powder or a metal powder or both. In this connection, a wall of the first tunnel is in one embodiment first wetted with a highly fluid paste and subsequently a less fluid paste by comparison with the highly fluid paste is introduced into the first tunnel. In this way, in one embodiment, a layer system of highly fluid and less fluid paste is formed in the first tunnel in radial direction, with the highly fluid paste wetting the tunnel wall. This in one embodiment improves a connection between the tunnel wall and the introduced paste and/or the first constituent formed therefrom by firing.

An inventive embodiment 7 of the method 1 is designed according to one of embodiments 1 to 4, wherein in method step a) the providing of the first ceramic precursor layer includes i) providing an unfilled first ceramic precursor layer, comprising the first layer surface and the further layer surface, wherein the first layer surface is opposite the further layer surface, wherein the first layer surface includes the first opening, wherein the further layer surface includes the further opening, wherein the first opening and the further opening are connected by the first tunnel;

ii) providing the second composition;

iii) introducing the second composition through the first opening into the first tunnel in at least one introduction step, wherein after each introduction step an introduced portion of the second composition is dried;
iv) providing the first composition; and
v) overlaying the second composition in the first tunnel with the first composition in at least one introduction step, wherein after each introduction step an introduced portion of the first composition is dried.

In method step v), the second composition is in one embodiment overlaid in so many introduction steps with so many portions of the first composition as are necessary in order to fill the first tunnel completely and to occlude the first opening flush to the further layer surface.

An inventive embodiment 8 of the method 1 is designed according to embodiment 7, wherein in method step iii) the second composition is introduced in at least one first introduction step and a further introduction step through the first opening into the first tunnel, wherein in the first introduction step first of all a first portion of the second composition is introduced and thereafter in the further introduction step a further portion of the second composition is introduced, wherein the first portion of the second composition has a second first viscosity, wherein the further portion of the first composition has a second further viscosity, wherein the second further viscosity is more than the second first viscosity.

The second further viscosity here is in one embodiment more by 40 Pa·s, in one embodiment by 50 Pa·s, in one embodiment by 60 Pa·s, than the second first viscosity. The first portion in one embodiment has a second first solids fraction and the further portion has a second further solids fraction, wherein the second further solids fraction is more than the second first solids fraction. The second further solids fraction here is in one embodiment more by at least 10 wt %, in one embodiment by at least 15 wt %, in one embodiment by at least 20 wt %, than the second first solids fraction. In one embodiment, a solid in this case is a powder. In one embodiment, a powder is a ceramic powder or a metal powder or both. In this connection, a wall of the first tunnel is in one embodiment first wetted with a highly fluid paste and subsequently a less fluid paste by comparison with the highly fluid paste is introduced into the first tunnel. In this way, in one embodiment, a layer system of highly fluid and less fluid paste is formed in the first tunnel in radial direction, with the highly fluid paste wetting the tunnel wall. This in one embodiment improves a connection between the tunnel wall and the introduced paste and/or the second constituent formed therefrom by firing.

An inventive embodiment 9 of the method 1 is designed according to one of embodiments 1 to 8, wherein the drying of the introduced portion includes heating of the introduced portion to a drying temperature in a range from 30 to 500° C., in one embodiment from 40 to 400° C., in one embodiment from 45 to 300° C., in one embodiment from 50 to 200° C., in one embodiment from 55 to 100° C., in one embodiment from 60 to 95° C., in one embodiment from 70 to 90° C., in one embodiment from 75 to 85° C.

An inventive embodiment 10 of the method 1 is designed according to one of embodiments 1 to 9, wherein the method after method step c) includes as a further method step
d) firing the first ceramic precursor layer and the second ceramic precursor layer, or the first ceramic precursor layer and the second ceramic precursor layer and the third ceramic precursor layer, or the first ceramic precursor layer and the second ceramic precursor layer and the third ceramic precursor layer and the at least one further ceramic precursor layer.

The first ceramic precursor layer in one embodiment includes n first tunnels, wherein each first tunnel is filled in the method of the embodiments in the manner described in the above embodiments for the first tunnel, wherein n is a natural number greater than 0, in one embodiment greater than 2, in one embodiment greater than 7, in one embodiment greater than 15, in one embodiment greater than 31, in one embodiment greater than 63, in one embodiment greater than 127, in one embodiment greater than 255, in one embodiment greater than 511. The second ceramic precursor layer in one embodiment includes n inventive second tunnels, wherein each second tunnel is filled in the method of the embodiments in the manner described in the above embodiments for the second tunnel, wherein n is a natural number greater than 0, in one embodiment greater than 2, in one embodiment greater than 7, in one embodiment greater than 15, in one embodiment greater than 31, in one embodiment greater than 63, in one embodiment greater than 127, in one embodiment greater than 255, in one embodiment greater than 511. The third ceramic precursor layer includes n inventive third tunnels, wherein each third tunnel is filled in the method of the embodiments in the manner described in the above embodiments for the third tunnel, wherein n is a natural number greater than 0, in one embodiment greater than 2, in one embodiment greater than 7, in one embodiment greater than 15, in one embodiment greater than 31, in one embodiment greater than 63, in one embodiment greater than 127, in one embodiment greater than 255, in one embodiment greater than 511. In a further aspect of this design, it is possible for the mutually contacted ceramic precursor layers to be divided up before the firing in method step d), in such a way that the number n of the tunnels per ceramic precursor layer is reduced by a factor of at least 2, in one embodiment by a factor of at least 3, in one embodiment by a factor of at least 4, in one embodiment by a factor of at least 5.

An inventive embodiment 11 of the method 1 is designed according to embodiment 10, wherein in method step d)
A) in the firing of the first ceramic precursor layer from the second composition, a second constituent is obtained, wherein, in a further method step, the second constituent is electroconductingly connected to an electrical conductor; or
B) in the firing of the third ceramic precursor layer from the further second composition, a third constituent is obtained, wherein, in a further method step, the third constituent is electroconductingly connected to an electrical conductor; or
C) both.

In one embodiment, an electrical conductor is a wire or a solder or both. The electrical conductor is in one embodiment connected to the second constituent by one selected from the group consisting of bonding, welding and soldering, or a combination of at least two thereof.

A contribution to achieving at least one of the above is made by an embodiment 1 of a method 2, comprising as method steps:
a) providing an unfilled ceramic precursor layer comprising a first layer surface and a further layer surface,
    wherein the first layer surface is opposite the further layer surface,
    wherein the first layer surface includes a first opening,
    wherein the further layer surface includes a further opening, wherein the first opening and the further opening are connected by a tunnel;
b) providing a third composition,
wherein the third composition has a third composition metal fraction, based on the weight of the third composition;
c) providing a first composition,
wherein the first composition has a first composition metal fraction based on the weight of the first composition,
wherein the third composition metal fraction differs by at least 3 wt %, in one embodiment by at least 7 wt %, in one embodiment by at least 15 wt %, from the first composition metal fraction;
d) providing a second composition,
wherein the second composition has a second composition metal fraction, based on the weight of the second composition,
wherein the second composition metal fraction differs by at least 3 wt %, in one embodiment by at least 7 wt %, in one embodiment by at least 15 wt %, from the first composition metal fraction;
e) introducing the third composition through the first opening into the tunnel in at least one introduction step, wherein after each introduction step an introduced portion of the third composition is dried;
f) overlaying the third composition in the tunnel with the first composition in at least one introduction step,
wherein the first composition is introduced through the first opening into the tunnel,
wherein after each introduction step an introduced portion of the first composition is dried;
g) overlaying the first composition in the tunnel with the second composition in at least one introduction step,
wherein the second composition is introduced through the first opening into the tunnel,
wherein after each introduction step an introduced portion of the second composition is dried; and
firing the ceramic precursor layer comprising the first composition, the second composition and the third composition.

In one embodiment, drying of an introduced portion includes heating of the introduced portion to a drying temperature in a range from 30 to 500° C., in one embodiment from 40 to 400° C., in one embodiment from 45 to 300° C., in one embodiment from 50 to 200° C., in one embodiment from 55 to 100° C., in one embodiment from 60 to 95° C., in one embodiment from 70 to 90° C., in one embodiment from 75 to 85° C.

An inventive embodiment 12 of the method 1 is designed according to one of embodiments 1 to 11, and an embodiment 2 of the method 2 is designed according to embodiment 1, wherein one selected from the group consisting of the first composition, the second first composition, the third first composition, the second composition, and the further second composition, or a combination of at least two thereof, is a cermet paste.

A contribution to achieving at least one of the above is made by an embodiment 1 of a ceramic precursor 1, obtainable by the method 1 according to one of embodiments 1 to 12 or by the method 2 according to embodiment 1 or 2.

A contribution to achieving at least one of the above is made by an embodiment 1 of an apparatus 4, obtainable by the method 1 according to embodiment 10 or 11, or by the method 2 according to embodiment 1 or 2.

A contribution to achieving at least one of the above is made by an embodiment 1 of an electrical device 1, comprising a housing comprising a housing opening; wherein the housing opening borders the apparatus 1 according to one of embodiments 1 to 19, or borders the apparatus 4 according to embodiment 1. The apparatus in one embodiment occludes the housing opening with hermetic sealing.

An inventive embodiment 2 of the electrical device 1 is designed according to embodiment 1, wherein the electrical device is an implantable electrical medical device.

A contribution to achieving at least one of the above is made by an embodiment 1 of a use 1 of the apparatus 1 according to one of embodiments 1 to 19, or of the apparatus 4 according to embodiment 1, for electrically connecting an interior of a housing to an exterior of the housing. In one embodiment, a housing is hermetically sealed.

A contribution to achieving at least one of the above is made by an embodiment 1 of a use 2 of the ceramic precursor 1 according to embodiment 1 for producing an electrical feedthrough.

A contribution to achieving at least one of the above is made by an embodiment 1 of a method 3 comprising as method steps
a) providing the implantable electrical medical device according to embodiment 2 of the electrical device 1;
b) implanting the implantable electrical medical device into a eukaryotic organism.

A contribution to achieving at least one of the above is made by an embodiment 1 of a use 3 of the implantable electrical medical device according to embodiment 2 of the electrical device 1 in a therapy of a disease or a dysfunction or both.

Designs of constituents of one category of the embodiments, for example, but not exclusively of the apparatuses, of the methods and of the electrical device, are also exemplary for corresponding constituents or constituents of the same name in the other categories of the embodiments.

Cermet

In accordance with one embodiment, a "cermet" is a composite material of one or more ceramic materials in at least one metallic matrix, or a composite material of one or more metallic materials in at least one ceramic matrix, or both. To produce a cermet it is possible, for example, to use a mixture of at least one ceramic powder and at least one metallic powder, it being possible for this mixture to be admixed, for example, at least with a vehicle, in one embodiment with a binder, and optionally at least with a solvent. A mixture of this kind composed of ceramic and metallic powders and binder is also referred to as a cermet paste. The ceramic powder or powders of this cermet in one embodiment have an average particle size of less than 10 µm, in one embodiment less than 5 µm, in one embodiment less than 3 µm. The metallic powder or powders of the cermet in one embodiment an average particle size of less than 15 µm, in one embodiment less than 10 µm, in one embodiment less than 5 µm. The average particle size considered here is, for example, the median or $D_{50}$ of the particle size distribution. The $D_{50}$ describes the figure at which 50% of the particles of the ceramic powder and/or of the metallic powder are finer than the $D_{50}$. In one embodiment, cermet has a high specific conductivity. In any case the cermet ought to be electrically conductive.

The at least one ceramic component of a cermet of the embodiments include a ceramic of the embodiments. The at least one metallic component of a cermet of one embodiment includes one selected from the group consisting of platinum, iridium, niobium, palladium, iron, stainless steel, cobalt-chromium alloy, molybdenum, tantalum, tungsten, titanium, cobalt and zirconium or combination of at least two thereof. In one embodiment, a combination in this context is an alloy. In one embodiment, a stainless steel is a 316L stainless steel. An electrically conductive connection is generally produced in the cermet when the metal content is above the so-called percolation threshold, at which the metal particles in the sintered cermet are connected to one another at least pointwise, thus permitting an electrical conduction. For this purpose, from experience, depending on the material selected, the metal content ought to be at least 25 vol %, in one embodiment at least 32 vol %, in one embodiment at least 38 vol %, based in each case on the total volume of the cermet.

Cermet Paste

In one embodiment, a cermet paste includes
   a) a metallic component, in one embodiment at least one metal powder, at a fraction in a range from 30 to 92 wt %, in one embodiment from 40 to 88 wt %, in one embodiment from 60 to 85 wt %, based in each case on the weight of the cermet paste,
   b) a ceramic component, in one embodiment at least one ceramic powder, in one embodiment at least one metal oxide, at a fraction in a range from 3 to 25 wt %, in one embodiment from 4 to 20 wt %, in one embodiment from 5 to 15 wt %, based in each case on the weight of the cermet paste, and
   c) a vehicle as the balance constituent up to 100 wt %, based on the weight of the cermet paste.

Compositions

In one embodiment, a composition of the embodiments, and in one embodiment, a first composition, is a cermet paste. This is also true, for example, of all further first compositions. A further second composition or further second composition or both is a metal paste. In one embodiment, a metal paste includes a metal fraction in a range from 70 to 95 wt %, in one embodiment from 75 to 90 wt %, in one embodiment from 80 to 90 wt %, based on the weight of the metal paste, and a vehicle as the balance constituent up to 100 wt %, based on the weight of the metal paste. In one embodiment, the fraction of a ceramic component here, in one embodiment of a ceramic powder and in one embodiment of a metal oxide, is below 3 wt %, based on the weight of the metal paste.

Ceramic Precursor Layer

In one embodiment, a ceramic precursor layer is a foil. In one embodiment, a ceramic precursor layer has a thickness in a range from 50 to 2000 µm, in one embodiment from 100 to 800 µm, in one embodiment from 200 to 600 µm, in one embodiment from 300 to 500 µm, in one embodiment from 350 to 450 µm. The ceramic precursor layers contacted with one another are in one embodiment divided up into smaller units before the firing in method step d), in such a way as to reduce, in one embodiment to minimize, the incidence of thermal stresses within the ceramic precursor layers in the course of firing.

Vehicle

In one embodiment, vehicles are inorganic vehicles and organic vehicles. In one embodiment, an inorganic vehicle is water. In one embodiment, an organic vehicle is a solution, an emulsion or a dispersion based on one or more solvents, in one embodiment on an organic solvent, which ensures that the constituents of the paste are present in emulsion or dispersion. In one embodiment, an organic solvent ensures optimum stability of the paste constituents and endows the paste with a viscosity which permits effective printing of the paste. In one embodiment, an organic vehicle includes:
   a) a binder, in one embodiment at a fraction in a range from 1 to 10 wt %, in one embodiment from 2 to 8 wt %, in one embodiment from 3 to 7 wt %, based on the weight of the vehicle,
   b) a surfactant, in one embodiment at a fraction in a range from 0 to 10 wt %, in one embodiment from 0 to 8 wt %, in one embodiment from 0.01 to 6 wt %, based on the weight of the vehicle,
   c) one or more solvents, the fraction being dictated by the fractions of the other components of the vehicle,
   d) optionally additives, in one embodiment at a fraction in a range from 0 to 15 wt %, in one embodiment from 0 to 13 wt %, in one embodiment from 5 to 11 wt %, based on the weight,
where the figures in wt % add up to 100 wt %. In one embodiment, an organic vehicle is one which contributes to effective printability of the paste.

Binder

In one embodiment, binders contribute to an appropriate stability, printability, viscosity or appropriate sintering behaviour of the paste. Binders are known in the prior art. All binders which appear to the skilled person to be suitable for inventive use in an organic vehicle can be used. In one embodiment, binders are polymer binders, monomer binders and binders which are a combination of polymers and monomers. Polymer binders may also be copolymers, in which case at least two monomer units are included in a single molecule. In one embodiment, polymer binders carry a functional group in their polymer main chain, have a functional group outside the polymer main chain, or have functional groups in the polymer main chain and outside. In one embodiment, polymers which carry a functional group in their polymer main chain are, for example, polyesters, substituted polyesters, polycarbonates, substituted polycarbonates, polymers having cyclic groups in the polymer main chain, polysaccharides, substituted polysaccharides, polyurethanes, substituted polyurethanes, polyamides, substituted polyamides, phenolic resins, substituted phenolic resins, copolymers of the monomers of one or more of the aforementioned polymers, optionally with other comonomers, or a combination of at least two of the above. In one embodiment, polymers having cyclic groups in the main chain are, for example, polyvinyl butyrate (PVB) and its derivatives, and polyterpineol and its derivatives, or mixtures of the above. In one embodiment, polysaccharides are, for example, cellulose and alkyl derivatives thereof, in one embodiment, methylcellulose, ethylcellulose, propylcellulose, butylcellulose, and also derivatives thereof and mixtures of at least two of the above. In one embodiment, polymers which carry a functional group outside the main chain are those which carry amide groups, which carry acid groups and/or ester groups, often called acrylic resins, or polymers which carry a combination of the aforesaid groups. In one embodiment, polymers which carry an amide group outside the main chain are, for example, polyvinylpyrrolidone (PVP) and its derivatives. In one embodiment, polymers which carry an acid group and/or ester group outside the main chain are, for example, polyacrylic acid and its derivatives, polymethacrylic acid (PMA) and its derivatives or polymethylmethacrylate (PMMA) and its derivatives, or mixtures of the above. In one embodiment, monomeric binders are ethylene glycol-based monomers, terpineol resins and also rosin derivatives, or mixtures of the above. In one embodiment, ethylene glycol-based monomers are those having ether groups, ester groups or those having ether groups and ester groups, in one embodiment ether groups here being methyl, ethyl, propyl, butyl, pentyl, hexyl and higher alkyls, and in one embodiment ester groups being acetates and alkyl derivatives thereof, in one embodiment ethylene glycol monobutyl ether monoacetates, or mixtures of the above. In one embodiment, binders are ethylcellulose and its derivatives and also mixtures with further binders from those listed above and also others.

Surfactant

In one embodiment, surfactants contribute to appropriate stability, printability, viscosity, or appropriate sintering behaviour of the paste. Surfactants are known in the prior art. All surfactants that appear to the skilled person to be suitable for inventive use in an organic vehicle can be used. In one embodiment, surfactants are based on linear chains, branched chains, aromatic chains, fluoridated chains, siloxane chains, polyether chains, or combinations of at least two thereof. In one embodiment, surfactants are single-chain, double-chain or polychain. In one embodiment, surfactants have non-ionic, anionic, cationic or zwitterionic ends. In one embodiment, surfactants are polymeric or monomeric or a mixture of both. In one embodiment, surfactants may have pigment affinity groups, in one embodiment hydroxyl-functional carboxylic esters with pigment affinity groups (for example DISPERBYK® 108, manufactured by BYK USA, Inc.), acrylate copolymers having pigment affinity groups (for example DISPERBYK®116, manufactured by BYK USA, Inc.), modified polyethers having pigment affinity groups (for example TEGO® DISPERS 655, manufactured by Evonik Tego Chemie GmbH), and other surfactants with groups of high pigment affinity (for example TEGO® DISPERS 662 C, manufactured by Evonik Tego Chemie GmbH). In one embodiment, polymers are polyethylene glycol and its derivatives, and alkylcarboxylic acid and derivatives or salts thereof, or mixtures of at least two of these. In one embodiment, polyethylene glycol is poly(ethylene glycol)acetic acid. In one embodiment, alkylcarboxylic acids are those having fully saturated or singularly or multiply unsaturated alkyl chains, or mixtures of at least two thereof. In one embodiment, carboxylic acids having saturated alkyl chains are those having alkyl chain lengths in a range from 8 to 20 carbon atoms, in one embodiment $C_9H_{19}COOH$ (capric acid), $C_{11}H_{23}COOH$ (lauric acid), $C_{13}H_{27}COOH$ (myristic acid), $C_{15}H_{31}COOH$ (palmitic acid), $C_{17}H_{35}COOH$ (stearic acid), or mixtures of at least two thereof. In one embodiment, carboxylic acids with unsaturated alkyl chains are $C_{18}H_{34}O_2$ (oleic acid) and $C_{18}H_{32}O_2$ (linoleic acid).

Solvent

In one embodiment, a solvent is a paste component which is removed substantially from the paste in the course of firing. The fraction of the solvent in the paste is in one embodiment reduced in the course of firing by at least 80 wt %, in one embodiment by at least 95 wt %, based on the weight of the paste or of the fired constituent relative to before firing. In one embodiment, solvents contribute to appropriate stability, printability, viscosity, or appropriate sintering behaviour of the paste. Solvents are known in the prior art. All solvents which appear to the skilled person to be suitable for inventive use in an organic vehicle can be used. In one embodiment, a solvent is in the form of a liquid at room temperature under atmospheric pressure (298.15 K, 100 kPa). In one embodiment, a solvent has a boiling temperature above 90° C. and a melting temperature above −20° C. In one embodiment, a solvent is a polar or apolar, protic or aprotic, aromatic or non-aromatic or ionic liquid. In one embodiment, solvents are monoalcohols, dialcohols, polyalcohols, monoesters, diesters, polyesters, monoethers, diethers, polyethers, solvents comprising one or at least two functional groups of these categories, optionally comprising functional groups of other categories, in one embodiment cyclic groups, aromatic groups, unsaturated bonds, alcohol groups in which one or at least two oxygen atoms have been replaced by heteroatoms, ether groups in which one or at least two oxygen atoms have been replaced by heteroatoms, ester groups in which one or at least two oxygen atoms have been replaced by heteroatoms, and mixtures of at least two thereof. In one embodiment, esters here are dialkyl esters of adipic acid, with in one embodiment alkyl constituents being methyl, ethyl, propyl, butyl, pentyl, hexyl and higher alkyl groups, or mixtures of at least two thereof, in one embodiment dimethyl adipate, and mixtures of two or more adipic esters. In one embodiment, ethers are diethers, in one embodiment dialkyl ethers of ethylene glycol, with in one embodiment alkyl constituents being methyl, ethyl, propyl, butyl, pentyl, hexyl and higher alkyl groups or mixtures of at least two thereof, and mixtures of two diethers. In one embodiment, alcohols are primary, secondary and tertiary alcohols, or a mixture of two or more alcohols. In one embodiment, alcohol is terpineol and derivatives thereof. In one embodiment, alcohols which include two or more functional groups are 2,2,4-trimethyl-1,3-pentanediol monoisobutyrate, also called Texanol, and derivatives thereof, 2-(2-ethoxyethoxy)ethanol, also called carbitol, alkyl derivatives thereof, in one embodiment methyl-, ethyl-, propyl-, butyl-, pentyl- and hexylcarbitol, in one embodiment hexylcarbitol or butylcarbitol, and acetate derivatives thereof, in one embodiment butylcarbitol acetate, or mixtures of at least two of the above.

Additives in the Organic Vehicle

In one embodiment, additives in the organic vehicle are different from the aforementioned components of the vehicle. In one embodiment, additives contribute to appropriate stability, printability, viscosity, or appropriate sintering behaviour of the paste. The vehicle additives are known in the prior art. All additives which appear to the skilled person to be suitable for inventive use in an organic vehicle can be used. In one embodiment, additives are thixotropic agents, viscosity regulators, stabilizers, inorganic additives, thickeners, emulsifiers, dispersants and pH regulators. In one embodiment, thixotropic agents are carboxylic acid derivatives, in one embodiment fatty acid derivatives. In one embodiment, fatty acid derivatives are $C_9H_{19}COOH$ (capric acid), $C_{11}H_{23}COOH$ (lauric acid), $C_{13}H_{27}COOH$ (myristic acid), $C_{15}H_{31}COOH$ (palmitic acid), $C_{17}H_{35}COOH$ (stearic acid), $C_{18}H_{34}O_2$ (oleic acid) and $C_{18}H_{32}O_2$ (linoleic acid), or mixtures of at least two thereof. In one embodiment, a mixture comprising fatty acid derivatives is castor oil.

Metal

Contemplated here are all metals familiar to the skilled person and possessing not only conductivity but also high compatibility with eukaryotic tissue. In one embodiment, a metal is selected from the group consisting of platinum, iridium, niobium, palladium, iron, stainless steel, cobalt-chromium alloy, molybdenum, tantalum, tungsten, titanium, cobalt and zirconium, or a combination of at least two thereof. In one embodiment, a combination here is an alloy. In one embodiment, a stainless steel is a 316L stainless steel. In one embodiment, a metal is biocompatible. In one embodiment, an alloy is biocompatible.

Ceramic

In one embodiment, a ceramic may be any ceramic which the skilled person would select for use in accordance with the embodiments. The ceramic is in one embodiment selected from the group consisting of an oxide ceramic, a silicate ceramic, a non-oxide ceramic or a mixture of at least two thereof.

The oxide ceramic is in one embodiment selected from the group consisting of a metal oxide, a semimetal oxide or a mixture thereof. The metal of the metal oxide may be selected from the group consisting of aluminium, beryllium, barium, calcium, magnesium, sodium, potassium, iron, zirconium, titanium or a mixture of at least two thereof. The metal oxide is in one embodiment selected from the group consisting of aluminium oxide ($Al_2O_3$), magnesium oxide (MgO), zirconium oxide ($ZrO_2$), yttrium oxide ($Y_2O_3$), aluminium titanate ($Al_2TiO_5$), a piezoceramic such as lead zirconate ($PbZrO_3$), lead titanate ($PbTiO_3$) and lead zirconate titanate (PZT), or a mixture of at least two thereof. The semimetal of the semimetal oxide is in one embodiment selected from the group consisting of boron, silicon, arsenic, tellurium or a mixture of at least two thereof. In one embodiment, oxide ceramic includes one selected from the group consisting of zirconia-toughened alumina (ZTA- $Al_2O_3/ZrO_2$), yttrium-toughened zirconia (Y-TZP), barium (Zr, Ti) oxide, barium(Ce, Ti) oxide, or a combination of at least two thereof.

The silicate ceramic is in one embodiment selected from the group consisting of a steatite ($Mg_3[Si_4O_{10}(OH)_2]$), cordierite (Mg, $Fe^{2+})_2(Al_2Si)[Al_2Si_4O_{18}]$), mullite ($Al_2Al_{2+2x}Si_{2-2x}O_{10-x}$ with x=oxygen vacancies per unit cell), feldspar ($Ba,Ca,Na,K,NH_4)(Al,B,Si)_4O_8$) or a mixture of at least two thereof.

The non-oxide ceramic may be selected from the group consisting of a carbide, a nitride or a mixture thereof. The carbide may be selected from the group consisting of silicon carbide (SiC), boron carbide ($B_4C$), titanium carbide (TiC), tungsten carbide and cementite (Fe3C). The nitride may be selected from the group consisting of silicon nitride ($Si_3N_4$), aluminium nitride (AlN), titanium nitride (TiN), silicon aluminium oxynitride (SIALON) or a mixture of at least two thereof. In one embodiment, non-oxide ceramic is sodium potassium niobate.

Biocompatible Material

In one embodiment, a biocompatible material is one selected from the group consisting of biotolerant, bioinert and bioactive or a combination of at least two thereof.

Constituents

The tunnel filling which includes the constituents is in one embodiment in one-piece form. In this case, in one embodiment, the constituents have been fired jointly to form one piece. The constituents of a tunnel filling in one embodiment form a layer construction in which the constituents are present as layers overlaying one another. In one embodiment, a first constituent has a first electrical conductivity in a range from $1 \cdot 10^3$ to $1 \cdot 10^6$ S/m, in one embodiment from $10 \cdot 10^3$ to $5 \cdot 10^5$ S/m, in one embodiment from $5 \cdot 10^4$ to $5 \cdot 10^5$ S/m. In one embodiment, a second constituent or a third constituent or, in one embodiment, both has or have a second or third electrical conductivity, respectively, in a range from $1 \cdot 10^3$ to $1 \cdot 10^7$ S/m, in one embodiment from $10 \cdot 10^3$ to $1 \cdot 10^7$ S/m, in one embodiment from $1 \cdot 10^5$ to $1 \cdot 10^7$ S/m. In one embodiment, a ceramic body has a further electrical conductivity in the range from $1 \cdot 10^{-6}$ to $1 \cdot 10^{-5}$ S/m, in one embodiment from $10 \cdot 10^{-6}$ to $50 \cdot 10^{-4}$ S/m, in one embodiment from $18 \cdot 10^{-6}$ to $18 \cdot 10^{-4}$ S/m.

Hermetically Sealed

In one embodiment, a tunnel of the apparatus is occluded with hermetic sealing. In one embodiment, an apparatus or an electrical device is hermetically sealed. In the context of one embodiment, the concept of "hermetic sealing/hermetically sealed" may mean that in the context of service as intended, within customary periods of time (for example 5 to 10 years), moisture or gases or both cannot be exchanged, or can be exchanged only minimally, through the hermetically sealed body between inside and outside. A physical parameter which may be used to describe, for example, the permeation of gases or moisture or both through the body is the so-called leakage rate, which can be determined by means of leak tests, for example. Such leak tests may be carried out, for example, using helium leakage testers and/or mass spectrometers, and are specified in the standard Mil-STD-883G Method 1014. The maximum permissible helium leakage rate here is stipulated as a function of the interior volume of the body under test, in the present case, for example, the internal volume of the electrical device. According to the methods specified in MIL-STD-883G, Method 1014, in Section 3.1, and taking account of the volumes and cavities in the apparatuses under test that are present in the use of the present embodiments, these maximum permissible helium leakage rates may amount, for example, to from $1 \times 10^{-8}$ atm×$cm^3$/s to $1 \times 10^{-7}$ atm×$cm^3$/s. In the context of one embodiment, the term "hermetically sealed" may, for example mean that the electrical device or the apparatus of one embodiment, in an otherwise perfectly hermetically sealed housing, exhibits a helium leakage rate of less than $1 \times 10^{-7}$ atm×$cm^3$/s. In one embodiment, the helium leakage rate may be less than $1 \times 10^{-8}$ atm×$cm^3$/s, in one embodiment less than $1 \times 10^{-9}$ atm×$cm^3$/s.

For the purpose of standardization, the stated helium leakage rates may also be converted into the equivalent standard air leak rate. The definition of the equivalent standard air leak rate and the conversion are set out in the standard ISO 3530. In view of the nature of use of implantable therapeutic devices, their hermetic sealing and biocompatibility is generally one of the foremost requirements. The electrical device proposed here may be used, for example, in a body of a human or animal user, more particularly a patient. As a result, the device is generally exposed to a fluid of a body tissue of the body. It is therefore in general important that neither body fluid penetrates the device, nor fluids escape from the device. In order to ensure this, the device ought to have an as far as possible complete impermeability, for example, with respect to body fluids.

Isostatic Pressing

Isostatic pressing is the pressing of a workpiece wherein a difference in the pressures exerted on the workpiece from every spatial direction is as small as possible. In one embodiment, isostatic pressing takes place at a temperature of the workpiece to be pressed, in one embodiment of the ceramic precursor layers, in a range from 50 to 100° C., in one embodiment from 60 to 90° C., in one embodiment from 65 to 75° C. On isostatic pressing, a workpiece to be pressed, in one embodiment the ceramic precursor layers, is or are located in one embodiment in a liquid, in one embodiment an oil bath.

Contacting/Laminating

In one embodiment, a form of contacting is laminating. Laminating joins at least two layers or two surfaces firmly to one another. Laminating is accomplished in one embodiment by compressing. A laminate is produced accordingly, a laminate being a sheetlike assembly. In one embodiment, laminating includes isostatic pressing. In this case, two articles are joined firmly to one another when their rigid adhesion to one another exceeds Van der Waals forces.

Introducing/Overlaying

In one embodiment, introducing of a composition or a overlaying with a composition is accomplished as a knife coating or printing operation, or both, on the composition. In one embodiment, a printing is a screen printing or a stencil printing or both.

Firing

In one embodiment, the firing may be carried out in any furnace that appears to the skilled person to be suitable for the firing of a green compound. In one embodiment, a firing takes place in a chamber furnace. In one embodiment, a firing includes a maximum temperature in a range from 1000 to 2000° C., in one embodiment from 1250 to 1900° C., in one embodiment from 1510 to 1650° C. In one embodiment, a firing includes a holding time for the holding of a maximum temperature in a range from 0.3 to 10 h, in one embodiment from 0.5 to 7 h, in one embodiment from 1 to 5 h. In one embodiment, a firing is a sintering.

Sintering

In one embodiment, sintering or a sintering operation is generally understood to mean a method for manufacturing materials or workpieces in which pulverulent materials, in one embodiment one selected from the group consisting of fine-particle substances, ceramic substances and metallic substances, or a combination of at least two thereof, are heated and thereby joined. This operation may take place without external pressure on the substance to be heated, or may, for example, take place with increased pressure on the substance to be heated, as for example under a pressure of at least 2 bar, V higher pressures, as for example pressures of at least 10 bar, V at least 100 bar or even at least 1000 bar. The operation may take place, for example, completely or partly at temperatures below the melting temperature of the pulverulent materials, as for example at temperatures from 700° C. to 1400° C. The process may be carried out, for example, completely or partly in a die or in a mould, or both, allowing shaping to be combined with the sintering operation. Besides the pulverulent materials, a starting material for the sintering operation may include further materials, examples being one or more binders, or one or more solvents, or both. The sintering operation may take place in one step or else in two or more steps, and the sintering operation may be preceded, for example, by further steps, examples being one or more shaping steps, or one or more debindering steps, or both. The sintering or the sintering operation therefore corresponds to a firing operation. The sintering operation, especially for a cermet, may run in a manner comparable to a sintering operation used customarily for homogeneous powders. In the sintering process, for example, the material may be compacted at high temperature and, where appropriate, high pressure, so that the cermet is virtually dense, or has at most a closed porosity. Cermets are notable in general for particularly high hardness and wear resistance.

Drying

In one embodiment, drying includes a maximum temperature in a range from 30 to 500° C., in one embodiment from 40 to 400° C., in one embodiment from 45 to 300° C., in one embodiment from 50 to 200° C., in one embodiment from 55 to 100° C., in one embodiment from 60 to 95° C., in one embodiment from 70 to 90° C., in one embodiment from 75 to 85° C. In one embodiment, drying is carried out for at least 3 min, in one embodiment at least 4 min, in one embodiment at least 5 min, in one embodiment at least 7 min, in one embodiment at least 10 min.

Implantable Electrical Medical Device

In one embodiment, an implantable electrical medical device is a therapy device or a diagnosis device or both. In one embodiment, a therapy device is implantable into a heart. In one embodiment, a therapy device is a defibrillator or a pacemaker or both. In one embodiment, a pacemaker is one selected from the group consisting of a cardiac pacemaker, a bladder pacemaker, an intestinal pacemaker, a cerebral pacemaker, a respiratory pacemaker and a diaphragmatic pacemaker or a combination of at least two thereof. In one embodiment, a pacemaker is a cardiac pacemaker. In one embodiment, a cardiac pacemaker is a wireless cardiac pacemaker. In one embodiment, a diagnosis device is a biomonitor. In one embodiment, a biomonitor includes one selected from the group consisting of an ECG device, a Holter monitor, an event recorder and a loop recorder, or a combination of at least two thereof. In one embodiment, an ECG device is a long-term ECG device which in one embodiment stores data arising over a period of at least an hour. In one embodiment, a diagnosis device includes a transmitting means or a data memory or both. In one embodiment, a transmitting means is designed for wireless, in one embodiment telemetric, transmission of data, in one embodiment ECG data. In one embodiment, a wireless transmission of data is transmission by means of waves. In one embodiment, waves are longitudinal waves or transverse waves or both. In one embodiment, longitudinal waves are acoustic waves or sound waves or both. In one embodiment, transverse waves are electromagnetic waves. In one embodiment, electromagnetic waves are waves with the frequency of a mobile radio network or of Bluetooth or both. In one embodiment, a mobile radio network is a GSM network. A data memory selected may be any unit for the storage of data that the skilled person considers to be suitable for the storage of medical data, in one embodiment ECG data, in an implantable device. In one embodiment, a data memory is a magnetic memory or a flash memory or both. In one embodiment, an implantable electrical medical device includes an electrical pulse generator.

Electrical Pulse Generator

An electrical pulse generator is an electronic circuit or an electronic device or both which is designed for single or repeated delivery of an electrical voltage pulse for a short period of time. In one embodiment, an electrical voltage pulse is a direct current voltage pulse. In one embodiment, a voltage pulse has a maximum voltage of less than 24 V, in one embodiment less than 12 V, in one embodiment less than 10 V, in one embodiment less than 2.4 V. In one embodiment, a short period of time is shorter than 500 ms, in one embodiment shorter than 100 ms, in one embodiment shorter than 50 ms, and in one embodiment shorter than 10 ms.

Eukaryotic Tissue

In one embodiment, a eukaryotic tissue is an animal tissue or a human tissue or both.

Therapy/Disease/Dysfunction

In one embodiment, a therapy is a neurotherapy or a cardiac therapy or both. In one embodiment, a neurotherapy includes electrical stimulation of a nerve. In one embodiment, a cardiac therapy in one embodiment includes electrical stimulation of a heart. In one embodiment, a neurotherapy is one selected from the group consisting of deep brain stimulation (DBS), spinal cord stimulation, vagus nerve stimulation, sacral nerve stimulation and gastric or intestinal nerve stimulation, or a combination of at least two thereof. In one embodiment, a cardiac therapy is one selected from the group consisting of cardiac pacemaker therapy, ICD therapy, CRT-P therapy and CRT-D therapy, or a combination of at least two thereof. In one embodiment, a deep brain stimulation is a therapy of one selected from the group consisting of Alzheimer's, Parkinson's disease, tremor, depression, epilepsy, dystonia, obsessive-compulsive disorder, Tourette's syndrome, coma and trauma, or a combination of at least two thereof. In one embodiment, a spinal cord stimulation is a therapy of one selected from the group consisting of chronic back pain, post-discotomy syndrome, complex regional pain syndrome and therapy-resistant pain, in one embodiment due to ischaemia, or a combination of at least two thereof. In one embodiment, a vagus nerve stimulation is a therapy of one selected from the group consisting of epilepsy, depression and chronic heart failure (CHF), or a combination of at least two thereof. In one embodiment, a sacral nerve stimulation is a therapy of one selected from the group consisting of urinary incontinence, urinary retention, frequent urge to void, stool incontinence, idiopathic constipation, interstitial cystitis and a chronic anal fissure, or a combination of at least two thereof. In one embodiment, a gastric or intestinal nerve stimulation is a therapy of obesity. In one embodiment, a cardiac pacemaker therapy is a therapy of bradycardia or tachycardia or both. In one embodiment, an ICD therapy is a therapy of atrial fibrillation or ventricular tachycardia or both. In one embodiment, a CRT-P therapy is a therapy of a chronic heart failure. In one embodiment, a CRT-D therapy is a therapy of a heart failure-induced conduction disorder or ventricular dyssynchrony or both.

Measurement Methods

The following measurement methods were used in the context of the embodiments. Unless otherwise indicated, the measurements were carried out at an ambient temperature of 25° C., an ambient air pressure of 100 kPa (0.986 atm) and a relative atmospheric humidity of 50%.

Biocompatibility

The biocompatibility is determined according to the standard 10993-4:2002.

Electrical Conductivity

The electrical conductivity is measured using a commercial conductivity meter (GLF 100 Universal conductivity meter from GHM Messtechnik GmbH Standort Greisinger, Regenstauf, Germany).

Viscosity

The viscosity was measured with a Thermo Fischer Scientific Corp. "Haake Rheostress 6000", equipped with a MPC60 Ti baseplate and a C 20/0.5° Ti cone, using the "Haake RheoWin Job Manager 4.00.0003" software. First of all, the distance zero point was set. Then the paste for measurement, in a sample quantity sufficient for the measurement, was applied to the baseplate. The cone was guided into the measuring position with a distance gap of 0.026 mm, and excess material was removed using a spatula. The sample was conditioned at 25° C. for 3 minutes and the rotational measurement was started. The shear rate was raised over the course of 48 s in 24 equidistant measuring steps from 0 to 20 $s^{-1}$ and then raised further over the course of 312 s in 156 equidistant measuring steps to 150 $s^{-1}$. After a waiting time of 60 s at a shear rate of 150 $s^{-1}$, the shear rate was reduced over the course of 312 s and 156 equidistant measuring steps to 20 $s^{-1}$, and then lowered further over the course of 48 s in 24 equidistant measuring steps to 0 $s^{-1}$. The torque correction, pressure monitoring and moment of inertia correction were activated during the measurement. The viscosity is given by the measurement value at the shear rate of 100 $s^{-1}$ that was attained during the lowering of the shear rate.

Scanning Electron Microscopy (SEM)

The sample was cut to expose the area for investigation. In general the cut was made through the layers of the layered construction, and also as a longitudinal cut through a tunnel of the sample. Accordingly, a cross section through the layered structure and at the same time a lengthwise cut through the tunnel was produced. After cutting, the sample was introduced into a container filled with an embedding material, and was arranged in such a way that the area for analysis pointed upwards. The embedding material used was EpoFix (Struers GmbH), prepared by mixing in accordance with the usage instructions. After 8 hours of curing at room temperature, processing of the sample continued. In a first step, the sample was abraded using a Labopol-25 (Struers GmbH) and silicon carbide paper 180-800 (Struers GmbH) at 250 revolutions/minute. In a further step, the sample was polished using a Rotopol-2, equipped with a Retroforce-4, MD Piano 220 and MD allegro. The sample was investigated using a Zeiss Ultra 55 (Carl Zeiss AG), equipped with a field emission electrode, at an acceleration voltage of 20 kV and under a pressure of about $3 \times 10^{-6}$ mbar. In some cases the cuts were used to determine the elemental composition along a straight line through the various layers. A linear analysis (line scan) was carried out by an EDX measurement (energy-dispersive X-ray spectroscopy). For this purpose, an IncaPentaFETx3 was mounted on the Zeiss Ultra 55, and the software "The Microanalysis Suite Issue 18d+SP3" (both from Oxford Instruments) were used, with an aperture of 30 μm.

The embodiments are set out in more detail below with examples and drawings, the examples and drawings not implying any restriction of the embodiments. Furthermore, the schematic representations are not to scale.

Paste Formulas

Cermet Paste:

60 g of a platinum powder were mixed with 24 g of an $Al_2O_3$ powder and an organic, ethylcellulose-based vehicle and the mixture was homogenized on a 3-roll mill. Pastes obtained accordingly had viscosities in a range from 250 to 300 Pa·s and a fineness of grind (FoG) of less than 10 μm. The rheology of the paste was suitable for stencil printing.

Metal Paste:

100 g of a platinum powder were mixed with 10 g of an $Al_2O_3$ powder and an organic, ethylcellulose-based vehicle and the mixture was homogenized on a 3-roll mill. Pastes obtained accordingly had viscosities in a range from 250 to 300 Pa·s and a fineness of grind (FoG) of less than 10 μm. The rheology of the paste was suitable for stencil printing.

Paste Preparation

In detail, the pastes were made ready as follows: the components reported above were mixed manually in a glass flask. These premixed pastes were homogenized using an Exakt E80 3-roll mill (from EXAKT Advanced Technologies GmbH) with stainless steel rolls. This was done by passing the pastes repeatedly through the mill, with the width of the gaps between the rolls (gap 1 between the first and second rolls; gap 2 between the second and third rolls) being reduced in steps. It was possible to regulate the gaps between the rolls in terms of their width (distance control) or the pressure between the rolls (pressure control). The initial steps of grinding were carried out with distance control. The final steps of grinding were carried out with pressure control. The values below were used for the gaps in the stated grinding steps. Equal values were used in each case here for gap 1 and for gap 2.

Steps 1 and 2: distance control 20 μm
Steps 3 and 4: distance control 15 μm
Steps 5 and 6: distance control 10 μm
Steps 7 and 8: distance control 5 μm
Steps 9, 10 and 11: pressure control 10 N/mm
Steps 12, 13 and 14: pressure control 12.5 N/mm
Steps 15, 16 and 17: pressure control 15 N/mm Preparation of Green Ceramic Foils Green ceramic foils were used as ceramic precursors. For this purpose, 99.7%-pure $Al_2O_3$ foils (Keral 99 from Keramische Folien GmbH) with a thickness of 400 µm were used. Samples of the green compact foils were cut into squares of 90 mm×90 mm. Approximately circular holes having a diameter of 400 µm were punched into the foil samples using a mechanical punch (CPC923101 from Groz-Beckert KG) for 400 µm diameter in an automatic puncher (MP4150 punch from Unichem Industries Inc.). A minimum of 3 foil samples were prepared in this way.

Filling

The holes prepared as above were filled by means of a stencil from Christian Koenen GmbH and an EKRA Microtronic II printer (model M2H). The stencil thickness was 100 µm. The openings in the stencil had the same dimensions and positions as the holes punched into the green compact foil as described above. The pressure parameters were 50 N squeegee pressure, forward squeegee speed 25 mm/s, backward squeegee speed 25 mm/s, and snap-off 0.0 mm. The squeegee circle was set so that paste material was introduced both during the forward movement and during the backward movement. Filling of around 200 µm in thickness after printing (wet) and about 150 µm in thickness after drying was achieved.

In accordance with the filling step described above, first and second foil samples were initially partly filled with the metal paste. The filling step here was repeated only with enough frequency not to fully fill the hole in the foil. For the complete filling of the hole, further filling steps with the cermet paste were carried out. In addition, 1 to 5 further foil samples were filled fully with the cermet paste by multiple implementation of the filling step above.

Drying

10 Minutes after the filling of the samples, they were introduced into a HHG-2 dryer (from BTU International Inc.) and dried therein at 80° C. for 10 minutes.

Laminating

The 3 to 7 layers of green compact foil with holes filled as described above were stacked using a metal alignment tool and subjected to isostatic pressing in an oil bath at 70° C. with a pressure of 350 bar for 10 minutes (laminator CE-1 from Autoclave Engineers, a division of Snap-tite Inc.), to achieve the desired component thickness. In this stack, the first and second foil samples represented the outer layers in each case, and the metal paste fillings of these samples pointed outwards in each case and had between them a continuous cermet paste filling.

Firing

The laminate of green compact foils as obtained above was fired in a high-temperature chamber furnace (FHT-175-10-12 from Arnold Schroder Industrieöfen GmbH), suitable for a maximum temperature of 1750° C. and having a chamber size of 200 mm×250 mm×200 mm. The laminate was placed on a piece of porous ceramic (KERALPOR 99 from Keramische Folien GmbH) in the furnace chamber. The firing operation took place under standard atmospheric conditions. The temperature was raised from 25 to 450° C. at a rate of 30° C./h. The temperature was then kept constant at 450° C. for 5 h in order to burn off the organic components in the green compact laminate. The temperature was subsequently raised to a maximum temperature in a range from 1510 to 1650° C. at a rate of 450° C./h, and was held constant at this level for a holding time in a range from 1 to 5 hours. Thereafter the temperature was lowered to room temperature at a cooling rate of 450° C./h or the natural cooling rate, which was slower.

Aftertreatment

After having been fired, the samples were abraded and then cut to the desired dimensions with a laser.

FIG. 1a illustrates a diagrammatic cross section through an inventive apparatus 100. The apparatus 100 includes a ceramic body 101, which in turn includes a first surface 103 and a further surface 102. The ceramic body 101 consists of $Al_2O_3$. The first surface 103 is opposite the further surface 102. The first surface 103 and the further surface 102 are two end faces of the ceramic body 101. The first surface 103 includes a first opening 105, which is circularly round. The further surface 102 includes a further opening 104, which is likewise circular. The first opening 105 and the further opening 104 are connected by a cylindrical tunnel 106 extending through the ceramic body 101. The first opening 105 and the further opening 104 are end faces of the tunnel 106. The first opening 105, the further opening 104 and the tunnel 106 are immaterial features. They delimit a cavity in the ceramic body 101. The tunnel 106 is fully filled with a tunnel filling 106. The tunnel 106 is therefore also occluded by the tunnel filling 106. The tunnel 106 is occluded with hermetic sealing by the tunnel filling 106. The tunnel filling 106 consists of a first constituent 107 and a second constituent 108. The first constituent 107 and the second constituent are connected to one another; they are directly adjacent to one another. A surface of the tunnel filling 106 that faces the further opening 104 is a surface of the second constituent 108. Here, the second constituent 108 fully fills the further opening 104 and occludes the further opening 104 flush to the further surface 102. The first constituent 107 and the second constituent 108 are electrically conducting. The first constituent 107 is a cermet of 60 vol % $Al_2O_3$ and 40 vol % platinum, based in each case on the volume of the first constituent 107. The second constituent 108 is a cermet of 20 vol % $Al_2O_3$ and 80 vol % platinum, based in each case on the volume of the second constituent 108. It emerges that a first electrical conductivity of the first constituent is more by $1\times10^6$ S/m than a further electrical conductivity of the ceramic body 101. Furthermore, a second electrical conductivity of the second constituent 108 is more by $1\times10^5$ S/m than the first electrical conductivity. In this arrangement, the tunnel filling 106, composed of the first constituent 107 and the second constituent 108, and the ceramic body 101 are formed in one piece. The tunnel filling 106 and the ceramic body 101 were fired together from a green body. There is no subsequently generated inter-material connection between the tunnel filling 106 and the ceramic body 101 and between the first constituent 107 and the second constituent 108. The aforementioned components merely represent three-dimensional regions with different material compositions in the apparatus 100. The first constituent 107 forms a first constituent layer, which in the tunnel 106 overlays a second constituent layer, formed by the second constituent 108. The two constituent layers are adjacent to one another directly at a first constituent surface 109 of the first constituent 107 and at a second constituent surface 109 of the second constituent 108. The first constituent surface 109 here is concave and the second constituent surface 109 is convex.

Figure 1B:
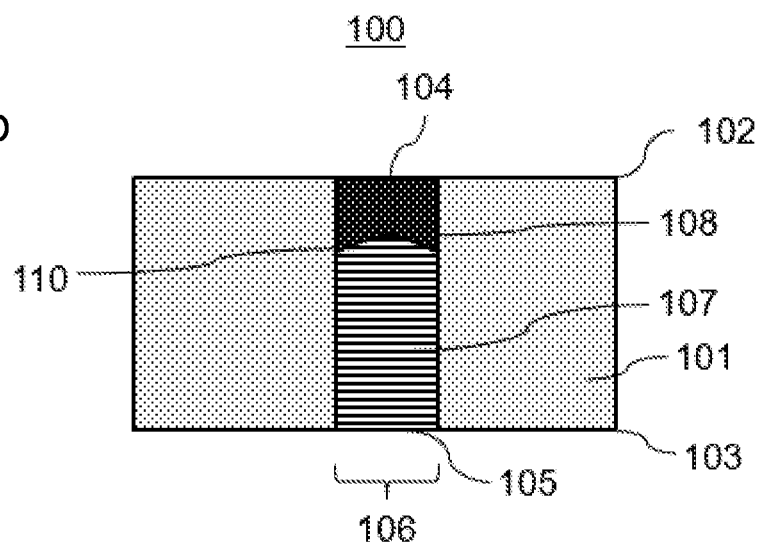
FIG. 1b illustrates a diagrammatic cross section through a further apparatus of one embodiment.

FIG. 1b illustrates a diagrammatic cross section through a further inventive apparatus 100. The apparatus 100 is identical to the apparatus 100 from FIG. 1a, apart from the fact that in FIG. 1b the first constituent surface 110 is convex and the second constituent surface 110 is concave.

Figure 2A:
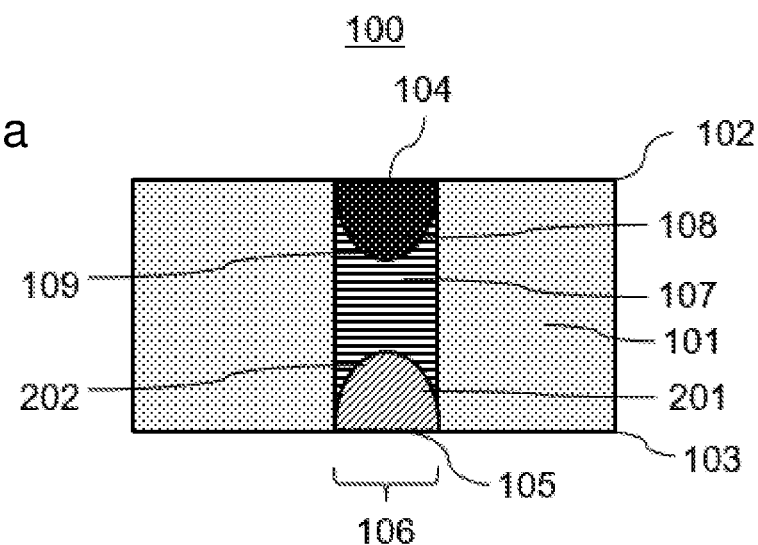
FIG. 2a illustrates a diagrammatic cross section through a further apparatus of one embodiment.

FIG. 2a illustrates a diagrammatic cross section through a further inventive apparatus 100. The apparatus 100 is identical to the apparatus 100 from FIG. 1a, apart from the fact that in FIG. 2a the tunnel filling 106 further includes a third constituent 201. A physical composition of the third constituent 201 is identical to that of the second constituent 108. Accordingly, the third constituent 201 as well as electrically conducting. The third constituent 201 and the first constituent 107 are connected to one another; they are directly adjacent to one another. A surface of the tunnel filling 106 that faces the first opening 105 is a surface of the third constituent 201. Here, the third constituent 201 fully fills the first opening 105 and occludes the first opening 105 flush to the first surface 103. A third electrical conductivity of the third constituent 201 is equal to the second electrical conductivity. In the tunnel 106, first constituent layer overlays a third constituent layer, formed by the third constituent 201. The first constituent layer and the third constituent layer are adjacent to one another directly at a further first constituent surface 202 of the first constituent 107 and at a third constituent surface 202 of the third constituent 201. In this case the further first constituent surface 202 is concave and the third constituent surface 202 is convex.

Figure 2B:
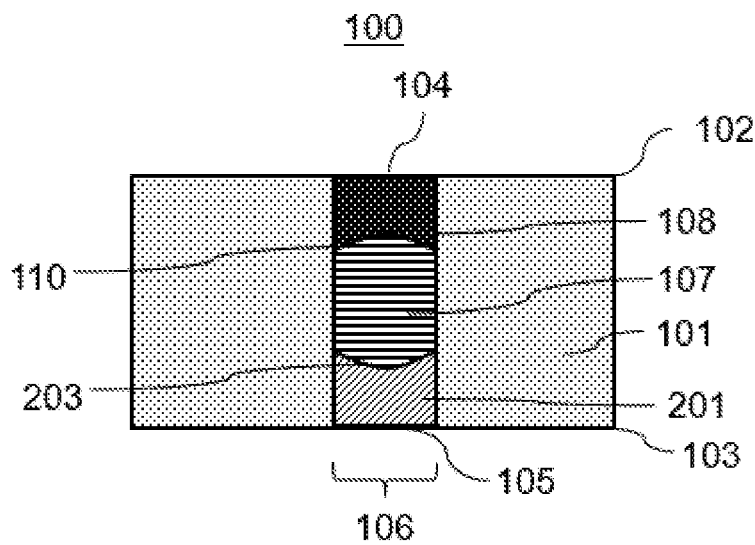
FIG. 2b illustrates a diagrammatic cross section through a further apparatus of one embodiment.

FIG. 2b illustrates a diagrammatic cross section through a further inventive apparatus 100. The apparatus 100 is identical to the apparatus 100 from FIG. 2a, apart from the fact that in FIG. 2b the first constituent surface 110 is convex and the second constituent surface 110 is concave, and also the further first constituent surface 203 is convex and the third constituent surface 203 is concave.

Figure 3:
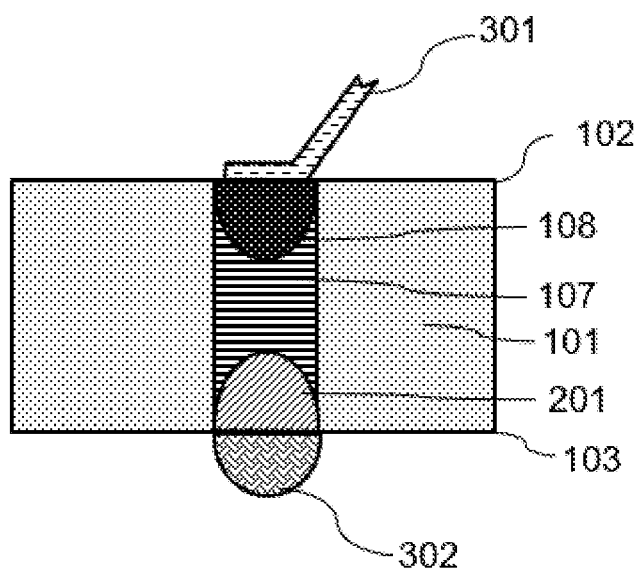
FIG. 3 illustrates a diagrammatic cross section through a further apparatus of one embodiment.

FIG. 3 illustrates a diagrammatic cross section through a further inventive apparatus 100. The apparatus 100 is identical to the apparatus 100 from FIG. 2a, apart from the fact that in FIG. 3 the second constituent 108 and third constituent 201 are each connected to an electrical conductor 301, 302. A bond wire 301 is bonded on the second constituent 108. A solder 302 is soldered on the third constituent 302. Via this solder, a wire or pin can be soldered on. Accordingly, the feedthrough element of the apparatus 100, hence in the present case the tunnel filling 106, can be electroconductively connected directly without a further component.

Figure 4:
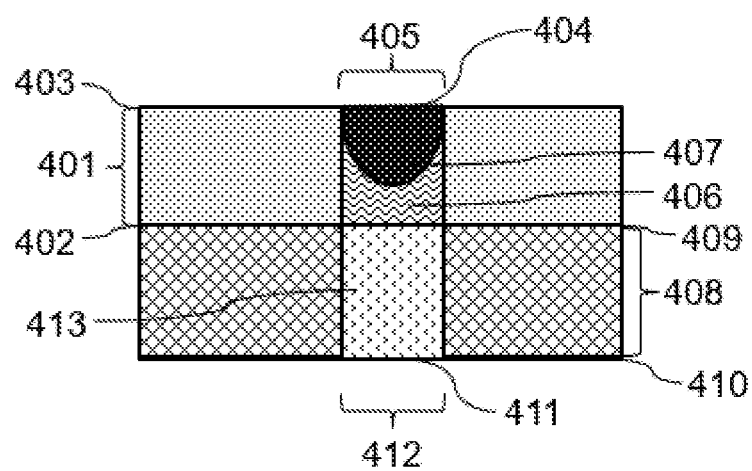
FIG. 4 illustrates a diagrammatic cross section through a further apparatus of one embodiment.

FIG. 4 illustrates a diagrammatic cross section through a further inventive apparatus 400. The apparatus 400 is a green body. The apparatus 400 includes a first ceramic precursor layer 401 and a second ceramic precursor layer 408. The first ceramic precursor layer 401 includes a first layer surface 402 and a further layer surface 403, the first layer surface 402 being opposite the further layer surface 403. Furthermore, the first layer surface 402 includes a first opening and the further layer surface 403 includes a further opening 404. The first opening and the further opening 404 are connected by a cylindrical first tunnel 405 extending through the first ceramic precursor layer 401. The first tunnel 405 includes a first tunnel filling 405 completely and is completely filled by the first tunnel filling 405 and therefore occluded. The first tunnel filling 405 consists of a first composition 406 and a second composition 407. The first composition 406 is a cermet paste consisting of 18 wt % of an $Al_2O_3$ powder, 73 wt % of a platinum powder and 9 wt % of an organic vehicle, based in each case on the weight of the first composition 406. The second composition 407 is a cermet paste consisting of 1.8 wt % of an $Al_2O_3$ powder, 89.2 wt % of a platinum powder and 9 wt % of an organic vehicle, based in each case on the weight of the second composition 407. The further opening 404 is filled flush to the further layer surface 403 and completely with the second composition 407 and occluded. The second ceramic precursor layer 408 includes a first layer surface 410 and a further layer surface 409, the first layer surface 410 being opposite the further layer surface 409. The first layer surface 410 includes a first opening 411, and a further layer surface 409 includes a further opening. The first opening 411 and the further opening are connected by a cylindrical second tunnel 412 extending through the second ceramic precursor layer 408. The second tunnel 412 is completely filled with a second tunnel filling 412 and occluded. The second tunnel filling 412 consists of a second first composition 413. The second first composition 412 is a cermet paste with a content identical to that of the first composition 406. The further layer surface 409 of the second ceramic precursor layer 408 is in contact with the first layer surface 402 of the first ceramic precursor layer 401 in such a way that the first tunnel filling 405 and the second tunnel filling 412 are in contact. Here, the first opening of the first ceramic precursor layer 401 and the further opening of the second ceramic precursor layer 408 lie congruently one over the other. The first ceramic precursor layer 401 and the second ceramic precursor layer 408 are laminated on one another and together with their respective tunnel filling 405, 412 they form a green body. The first ceramic precursor layer 401 and the second composition 406 and the second composition 407 are adjacent to one another along a convex surface of the second composition 407 and along a concave surface, complementary thereto, of the first composition 406.

Figure 5:
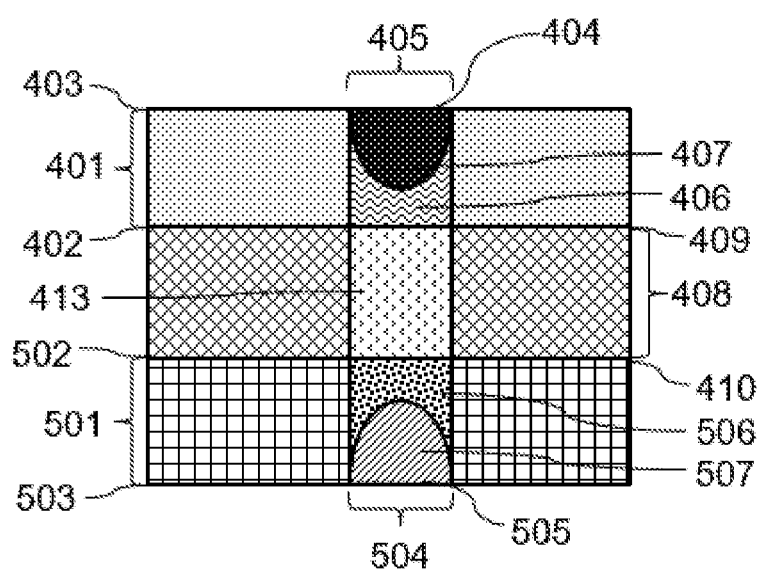
FIG. 5 illustrates a diagrammatic cross section through a further apparatus of one embodiment.

FIG. 5 illustrates a diagrammatic cross section through a further inventive apparatus 400. The apparatus 400 is identical to the apparatus 400 from FIG. 4, with the apparatus 400 of FIG. 5 further comprising a third ceramic precursor layer 501. The third ceramic precursor layer 501 includes a first layer surface 503 and a further layer surface 502, with the first layer surface 503 opposite the further layer surface 502. The first layer surface 503 includes a first opening 505, and the further layer surface 502 includes a further opening. The first opening 505 and the further opening are connected by a cylindrical third tunnel 504 extending through the third ceramic precursor layer 501. The third tunnel 504 includes a third tunnel filling 504 completely and is completely filled by the third tunnel filling 504 and occluded. The third tunnel filling 504 consists of a third first composition 506 and a further second composition 507. The further second composition 507 fills the first opening 505 completely and occludes it flush to the first layer surface 503. The third first composition 506 is a cermet paste with a content identical to that of the first composition 406. The further second composition 507 is a cermet paste with a content identical to that of the second composition 407. The first layer surface 410 of the second ceramic precursor layer 408 is overlaid by the further layer surface 502 of the third ceramic precursor layer 501. The third ceramic precursor layer 501 likewise has a layer thickness of 400 µm and is laminated onto the second ceramic precursor layer 408. Furthermore, the third first composition 506 and the further second composition 507 are along a concave surface, complementary thereto, of the third first composition 506.

Figure 6:
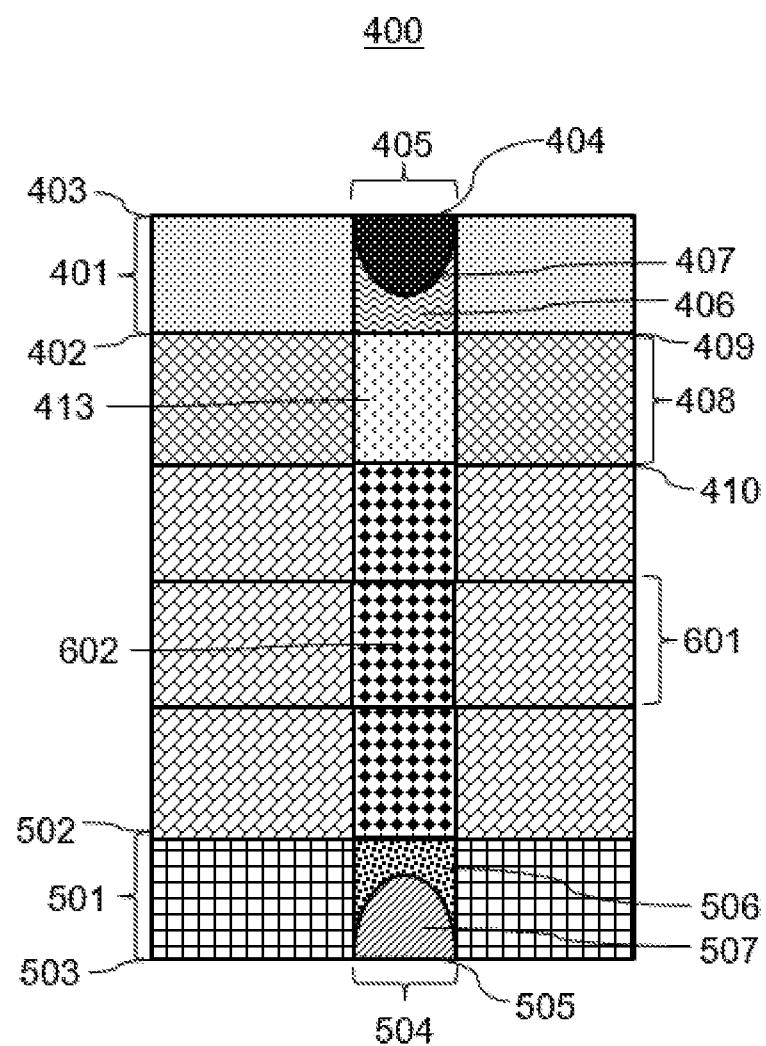
FIG. 6 illustrates a diagrammatic cross section through a further apparatus of one embodiment.

FIG. 6 illustrates a diagrammatic cross section through a further inventive apparatus 400. The apparatus 400 is identical to the apparatus 400 from FIG. 5, with the apparatus 400 of FIG. 6 further comprising three further ceramic precursor layers 601. The further ceramic precursor layer 601 are located between the second ceramic precursor layer 408 and the third ceramic precursor layer 501. All ceramic precursor layers 401, 408, 501 and 601 of the apparatus 400 are laminated to one another. The further ceramic precursor layers are each 400 µm thick and each include a further tunnel, which is filled with a cermet paste identical to the cermet paste which is the first composition 406. In the apparatus 400, all of the tunnels lie congruently one over another, and so from the further layer surface 403 of the first ceramic precursor layer 401 to the first layer surface 503 of the third ceramic precursor layer 501 there is a path composed of the second composition 407, the first composition 406, the second first composition 413, the further first compositions 602, the third first composition 506 and the further second composition 507.

Figure 7:
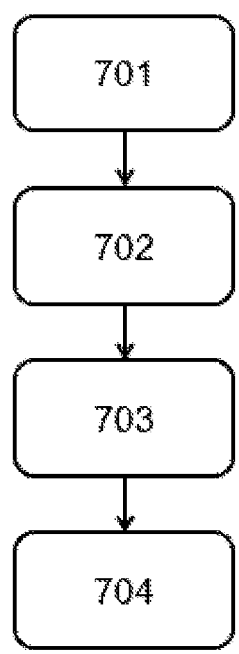
FIG. 7 illustrates a flow diagram of a method of one embodiment.

FIG. 7 illustrates a flow diagram of an inventive method 700. The method 700 includes as method step a) 701 the providing a first ceramic precursor layer, comprising a first layer surface and a further layer surface, the first layer surface being opposite the further layer surface. The first layer surface includes a first opening, and the further layer surface includes a further opening. The first opening and the further opening are connected by a first tunnel. The first tunnel includes a first tunnel filling at least partly, and is occluded by the first tunnel filling. The first tunnel filling includes a first composition and a second composition. A surface of the first tunnel filling, lying flush to the further layer surface in the further opening, is a surface of the second composition. The first composition has a first composition metal fraction, based on the weight of the first composition, and the second composition has a second composition metal fraction, based on the weight of the second composition. The second composition metal fraction is more by at least 10 wt % than the first composition metal fraction. The first ceramic precursor layer of the method 700 is identical to the first ceramic precursor layer 401 of FIG. 4. In a method step b) 702, a second ceramic precursor layer is provided, comprising a first layer surface and a further layer surface. The first layer surface is opposite the further layer surface. The first layer surface includes a first opening, and the further layer surface includes a further opening. The first opening and the further opening are connected by a second tunnel. The second tunnel includes a second tunnel filling and is occluded by the second tunnel filling. The second tunnel filling includes a second first composition. The second first composition has a second first composition metal fraction, based on the weight of the second first composition. The second composition metal fraction is more by at least 10 wt % than the second first composition metal fraction. The second ceramic precursor layer of the method 700 is identical to the second ceramic precursor layer 408 of FIG. 4. In a method step c), the further layer surface of the second ceramic precursor layer and the first layer surface of the first ceramic precursor layer are laminated to one another in such a way that the first tunnel filling and the second tunnel filling are contacted. Laminating takes place in an oil bath with the temperature of 70° C. as isostatic pressing. In a method step d) 704, the first ceramic precursor layer and the second ceramic precursor layer are jointly fired. The firing here includes a maximum temperature of 1650° C., which is maintained for a holding time of 2.5 h.

Figure 8:
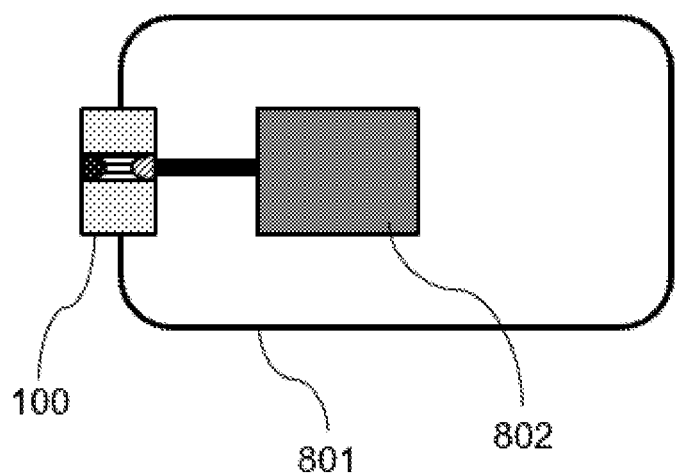
FIG. 8 illustrates a diagrammatic cross section through an electrical device of one embodiment.

FIG. 8 illustrates a diagrammatic cross section through an inventive electrical device 800. The electrical device 800 is an implantable cardiac pacemaker. The electrical device 800 includes a titanium housing 801 which includes a housing opening. The device 100 of FIG. 2a is welded into the housing opening via a titanium flange, which is not illustrated. The housing 801 is therefore closed with a hermetic seal. In its interior, the housing 801 includes an electrical pulse generator 802 which is electroconductingly connected via a bond wire 301, by bonding, to the third constituent 201 of the apparatus 100. The apparatus 100 is an electrical cermet feedthrough in the cardiac pacemaker.

Figure 9:
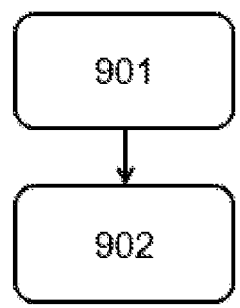
FIG. 9 illustrates a flow diagram of a further method of one embodiment.

FIG. 9 illustrates a flow diagram of a further inventive method 900. The method 900 includes a method step of a) providing the cardiac pacemaker 800 from FIG. 8, and a method step b) 902 of implanting the cardiac pacemaker 800 into a human patient.

Figure 10:
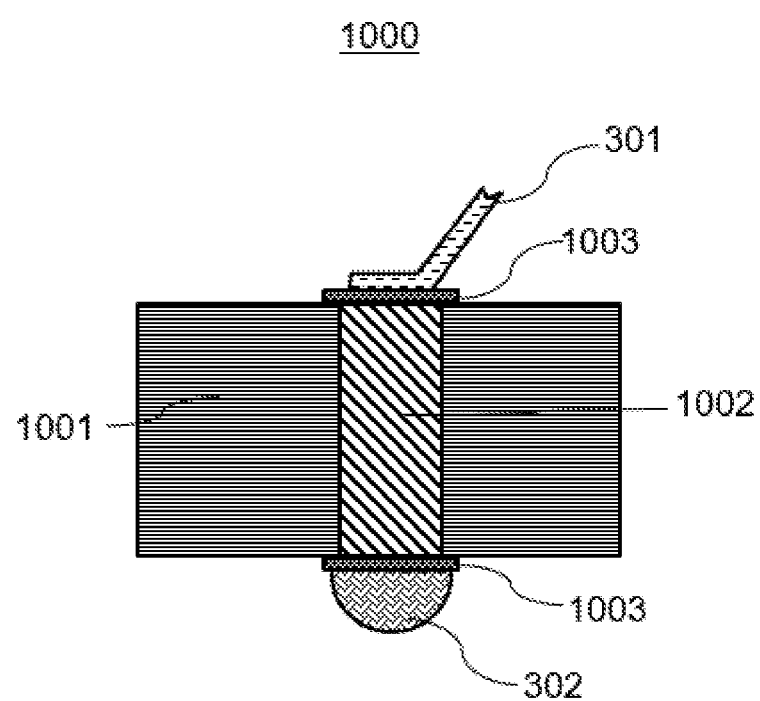
FIG. 10 illustrates a diagrammatic cross section through a non-inventive electrical feedthrough.

FIG. 10 illustrates a diagrammatic cross section through a non-inventive electrical feedthrough 1000. The feedthrough 1000 includes a ceramic ring 1001 as insulating body and a cermet 1002 as electrically conducting feedthrough element. The metal content of the cermet 1002 is selected such that optimum connection to the ceramic ring 1001 is achieved. In order to be able to connect the cermet electrically to a bond wire 301 and a solder 302, metal-containing surfaces 1003, with a metal content increased relative to the metal content of the cermet 1002, were applied to the cermet 1002. The feedthrough element, accordingly, is contacted via the additional metal-containing surfaces 1003.

Although specific embodiments have been illustrated and described herein, it will be appreciated by those of ordinary skill in the art that a variety of alternate and/or equivalent implementations may be substituted for the specific embodiments shown and described without departing from the scope of the present embodiments. This application is intended to cover any adaptations or variations of the specific embodiments discussed herein. Therefore, it is intended that these embodiments be limited only by the claims and the equivalents thereof.

What is claimed is:

1. An apparatus comprising a ceramic body comprising a first surface, a further surface and a tunnel extending therethrough;
   wherein the first surface is opposite the further surface;
   wherein the first surface comprises a first opening;
   wherein the further surface comprises a further opening;
   wherein the first opening and the further opening are connected by the tunnel;
   wherein the tunnel at least partly comprises a tunnel filling and is occluded by the tunnel filling;
   wherein the tunnel filling comprises a first constituent and a second constituent;
   wherein the first constituent comprises a cermet;
   wherein the first constituent and the second constituent are electroconductingly connected to one another;
   wherein a surface of the tunnel filling that faces the further opening is at least partly a surface of the second constituent;
   wherein the first constituent is characterized by a first electrical conductivity;
   wherein the second constituent is characterized by a second electrical conductivity;
   wherein the ceramic body is characterized by a further electrical conductivity;
   wherein the first electrical conductivity is more by at least $1 \cdot 10^5$ Siemens per meter than the further electrical conductivity; and
   wherein the second electrical conductivity differs from the first electrical conductivity by at least $5 \cdot 10^4$ Siemens per meter.

2. The apparatus of claim 1, wherein the second electrical conductivity is more than the first electrical conductivity.

3. The apparatus of claim 1, wherein the first constituent has a first metal fraction, based on the weight of the first constituent;
   wherein the second constituent has a second metal fraction, based on the weight of the second constituent;
   wherein the second metal fraction is more by at least 5 weight % than the first fraction.

4. The apparatus of claim 1, wherein the tunnel filling comprises a third constituent;
   wherein the third constituent is electrconductingly connected to the first constituent or to the second constituent or to both;
   wherein a surface of the tunnel filling that faces the first opening is at least partly a surface of the third constituent;
   wherein the third constituent is characterized by a third electrical conductivity;
   wherein the third electrical conductivity differs from the first electrical conductivity by at least $5 \cdot 10^4$ Siemens per meter.

5. The apparatus of claim 1, wherein one selected from a group consisting of the first constituent, the second constituent and the third constituent, or a combination of at least two thereof, is a cermet.

6. An electrical device comprising a housing comprising a housing opening;
   wherein the housing opening borders the apparatus of claim 1.

7. The electrical device of claim 6, wherein the electrical device is an implantable electrical medical device.

8. A use of the apparatus of claim 1 for electrically connecting an interior of a housing to an exterior of the housing.

9. An apparatus comprising a first ceramic precursor layer and a second ceramic precursor layer,
   a) wherein for the first ceramic precursor layer it is at least the case that:
      i) the first ceramic precursor layer comprises a first layer surface, a further layer surface and a first tunnel extending therethrough,
      ii) the first layer surface is opposite the further layer surface,
      iii) the first layer surface comprises a first opening,
      iv) the further layer surface comprise a further opening,
      v) the first opening and the further opening are connected by the first tunnel,
      vi) the first tunnel comprises a first tunnel filling at least partly and is occluded by the first tunnel filling,
      vii) the first tunnel filling comprises a first composition and a second composition,
      viii) a surface of the first tunnel filling that faces the further opening is at least partly a surface of the second composition,
      ix) the first composition has a first composition metal fraction, based on the weight of the first composition,
      x) the second composition has a second composition metal fraction, based on the weight of the second composition, and
      xi) the second composition metal fraction differs by at least 3 wt % from the first composition metal fraction,
   b) wherein for the second ceramic precursor layer it is at least the case that:
      i) the second ceramic precursor layer comprises a first layer surface, a further layer surface, and a second tunnel extending therethrough,
      ii) the first layer surface is opposite the further layer surface,
      iii) the first layer surface comprises a first opening,
      iv) the further layer surface comprises a further opening,
      v) the first opening and the further opening are connected by the second tunnel,
      vi) the second tunnel comprises a second tunnel filling at least partly and is occluded by the second tunnel filling,
      vii) the second tunnel filling comprises a second first composition,
      viii) the second first composition has a second first composition metal fraction, based on the weight of the second first composition, and
      ix) the second composition metal fraction differs by at least 3 wt % from the second first composition metal fraction,
   c) wherein the further layer surface of the second ceramic precursor layer is in contact with the first layer surface of the first ceramic precursor layer in such a way that the first tunnel filling and the second tunnel filling are in contact.

10. An apparatus comprising a ceramic precursor layer, wherein for the ceramic precursor layer it is at least the case that:
   a) the ceramic precursor layer comprises a first layer surface, a further layer surface and a tunnel extending therethrough,
   b) the first layer surface is opposite the further layer surface,
   c) the first layer surface comprises a first opening,
   d) the further layer surface comprises a further opening,
   e) the first opening and the further opening are connected by the tunnel,
   f) the tunnel comprises a tunnel filling at least partly and is occluded by the tunnel filling,
   g) the tunnel filling comprises a first composition, a second composition and a third composition,
   h) a surface of the tunnel filling that faces the further opening least partly a surface of the second composition,
   i) a surface of the tunnel filling that faces the first opening is at least partly a surface of the third composition,
   j) the first composition has a first composition metal fraction, based on the weight of the first composition,
   k) the second composition has a second composition metal fraction, based on the weight of the second composition,
   l) the third composition has a third composition metal fraction, based on the weight of the third composition, and
   m) the second composition metal fraction or the third composition metal fraction or both differs or differ by at least 3 weight % from the first composition metal fraction.

11. A method comprising:
   a) providing a first ceramic precursor layer comprising a first layer surface, a further layer surface and a first tunnel extending therethrough,
   wherein the first layer surface is opposite the further layer surface,
   wherein the first layer surface comprises a first opening,
   wherein the further layer surface comprises a further opening,
   wherein the first opening and the further opening are connected by the first tunnel,
   wherein the first tunnel at least partly comprises a first tunnel filling and is occluded by the first tunnel filling,
   wherein the first tunnel filling comprises a first composition and a second composition,
   wherein a surface of the first tunnel filling that faces the further opening is at least partly a surface of the second composition, wherein the first composition has a first composition metal fraction, based on the weight of the first composition, wherein the second composition has a second composition metal fraction, based on the weight of the second composition, wherein the second composition metal fraction differs by at least 3 wt % the first composition metal fraction;

b) providing a second ceramic precursor layer, comprising a first layer surface, a further layer surface and a second tunnel extending therethrough, wherein the first layer surface is opposite the further layer surface, wherein the first layer surface comprises a first opening, wherein the further layer surface comprises a further opening, wherein the first opening and the further opening are connected by the second tunnel, wherein the second tunnel at least partly comprises a second tunnel filling and is occluded by the second tunnel filling, wherein the second tunnel filling comprises a second first composition, wherein the second first composition has a second first composition metal fraction, based on the weight of the second first composition, wherein the second composition metal fraction differs by at least 3 wt % from the second first composition metal fraction; and c) contacting the further layer surface of the second ceramic precursor layer with the first layer surface of the first ceramic precursor layer, so that the first tunnel filling and the second tunnel filling are contacted.

12. The method of claim 11, wherein the method after method step c) further comprises:

d) firing the first ceramic precursor layer and the second ceramic precursor layer, or the first ceramic precursor layer and the second ceramic precursor layer and the third ceramic precursor layer, or the first ceramic precursor layer and the second ceramic precursor layer and the third ceramic precursor layer and the at least one further ceramic precursor layer.

13. An apparatus obtainable by the method of claim 12.

14. A ceramic precursor obtainable by the method of claim 11.

15. A use of the ceramic precursor of claim 14 for producing an electrical feedthrough.

16. A method comprising:

a) providing an unfilled ceramic precursor layer comprising a first layer surface, a further layer surface and a tunnel extending therethrough, wherein the first layer surface is opposite the further layer surface, wherein the first layer surface comprises a first opening, wherein the further layer surface comprises a further opening, wherein the first opening and the further opening are connected by the tunnel;

b) providing a third composition, wherein the third composition has a third composition metal fraction, based on the weight of the third composition;

c) providing a first composition, wherein the first composition has a first composition metal fraction based on the weight of the first composition, wherein the third composition metal fraction differs by at least 3 wt % from the first composition metal fraction;

d) providing a second composition, wherein the second composition has a second metal fraction, based on the weight of the second composition, wherein the second composition metal fraction differs by at least 3 wt % from the first composition metal fraction;

e) introducing the third composition through the first opening into the tunnel in at least one introduction step, wherein after each introduction step an introduced portion of the third composition is dried;

f) overlaying the third composition in the tunnel with the first composition in at least one introduction step, wherein the first composition is introduced through the first opening into the tunnel, wherein after each introduction step an introduced portion of the first composition is dried;

g) overlaying the first composition in the tunnel with the second composition in at least one introduction step, wherein the second composition is introduced through the first opening into the tunnel, wherein after each introduction step an introduced portion of the second composition is dried; and h) firing the ceramic precursor layer comprising the first composition, the second composition and the third composition.

* * * * *